United States Patent
Levene et al.

(10) Patent No.: US 7,181,122 B1
(45) Date of Patent: Feb. 20, 2007

(54) ZERO-MODE WAVEGUIDES

(75) Inventors: Michael J. Levene, Ithaca, NY (US);
Jonas Korlach, Ithaca, NY (US);
Stephen W. Turner, Ithaca, NY (US);
Harold G. Craighead, Ithaca, NY (US); Watt W. Webb, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/313,971

(22) Filed: Dec. 20, 2005

Related U.S. Application Data

(63) Continuation of application No. 11/151,807, filed on Jun. 13, 2005, now Pat. No. 7,013,054, which is a continuation of application No. 10/259,268, filed on Sep. 27, 2002, now Pat. No. 6,917,726.

(60) Provisional application No. 60/325,280, filed on Sep. 27, 2001.

(51) Int. Cl.
*G02B 6/10* (2006.01)

(52) U.S. Cl. ............... 385/132; 385/130; 385/146; 385/14; 385/125; 385/27; 385/28; 385/12

(58) Field of Classification Search ............ 385/12, 385/14, 27, 28, 123, 125, 129, 130, 131, 385/132, 146
See application file for complete search history.

(56) References Cited

U.S. PATENT DOCUMENTS 5,243,618 A * 9/1993 Dolezal et al. ............ 372/92
5,465,151 A  11/1995 Wybourne et al. ......... 356/361
5,677,769 A * 10/1997 Bendett ..................... 356/440
6,510,263 B1 * 1/2003 Maisenholder et al. ..... 385/37
6,528,780 B1 * 3/2003 Mitsuoka et al. .......... 250/216
6,573,089 B1  6/2003 Vann ...................... 435/287.2
6,713,672 B1 * 3/2004 Stickney ................... 174/382
6,917,726 B2 * 7/2005 Levene et al. ............. 385/12
7,013,054 B2 * 3/2006 Levene et al. ............. 385/12

(Continued)

FOREIGN PATENT DOCUMENTS

WO    WO 03/010289    2/2003

OTHER PUBLICATIONS

Craighead, H.G. Nanoelectromechanical Systems. Science. 2000; 290:1532-1535.

(Continued)

*Primary Examiner*—Brian M. Healy
(74) *Attorney, Agent, or Firm*—Wilson Sonsini Goodrich & Rosati

(57) ABSTRACT

The present invention is directed to a method and an apparatus for analysis of an analyte. The method involves providing a zero-mode waveguide which includes a cladding surrounding a core where the cladding is configured to preclude propagation of electromagnetic energy of a frequency less than a cutoff frequency longitudinally through the core of the zero-mode waveguide. The analyte is positioned in the core of the zero-mode waveguide and is then subjected, in the core of the zero-mode waveguide, to activating electromagnetic radiation of a frequency less than the cut-off frequency under conditions effective to permit analysis of the analyte in an effective observation volume which is more compact than if the analysis were carried out in the absence of the zero-mode waveguide.

31 Claims, 19 Drawing Sheets

U.S. PATENT DOCUMENTS

| | | |
|---|---|---|
| 2002/0110939 A1 | 8/2002 | Miki et al. .................. 438/12 |
| 2002/0180570 A1 | 12/2002 | Facer et al. ................. 333/239 |
| 2003/0137313 A1 | 7/2003 | Jannsen et al. ............. 324/646 |
| 2003/0174992 A1 | 9/2003 | Levene et al. .............. 385/129 |

OTHER PUBLICATIONS

Foquet, M.E. et al. Fabrication of Microcapillaries and Waveguides for Single Molecule Detection. SPIE 1998; 3258:(0277-786X) 141-147.

Jackson, J. D. Classical Electrodynamics. Second Edition. John Willey and Sons (Cover pages and table of contents).

Lopez, A.G. et al. Subwavelength Surface-Relief Gratings Fabricated by Microcontact Printing of Self-Assembled Monolayers. Applied Optics. 2001; 40:(13) 2068-2075.

Dorre, et al. Highly efficient single molecule detection in microstructures. J. Biotechnol. 2001; 86(3):225-36.

Heinze, et al. Two-photon fluorescence coincidence analysis: rapid measurements of enzyme kinetics. Biophys J. 2002; 83(3):1671-81.

Kang, et al. Investigations of Potential-Dependent Fluxes of Ionic Permeates in Gold Nanotubule Membranes Prepared via the Template Method. Langmuir. 2001; 17(9):2756-2759.

McDonald, et al. Fabrication of a configurable, single-use microfluidic device. Anal Chem. 2001; 73(23):5645-50.

Schwille, P., et al. Dual-Color Fluorescence Cross-Correlation Spectroscopy for Multicomponent Diffusional Analysis in Solution. Biophysical Journal. 1997; 72:1878-86.

Weiss, S. Fluorescence Spectroscopy of Single Biomolecules. Science. 1999; 283:1676-83.

\* cited by examiner

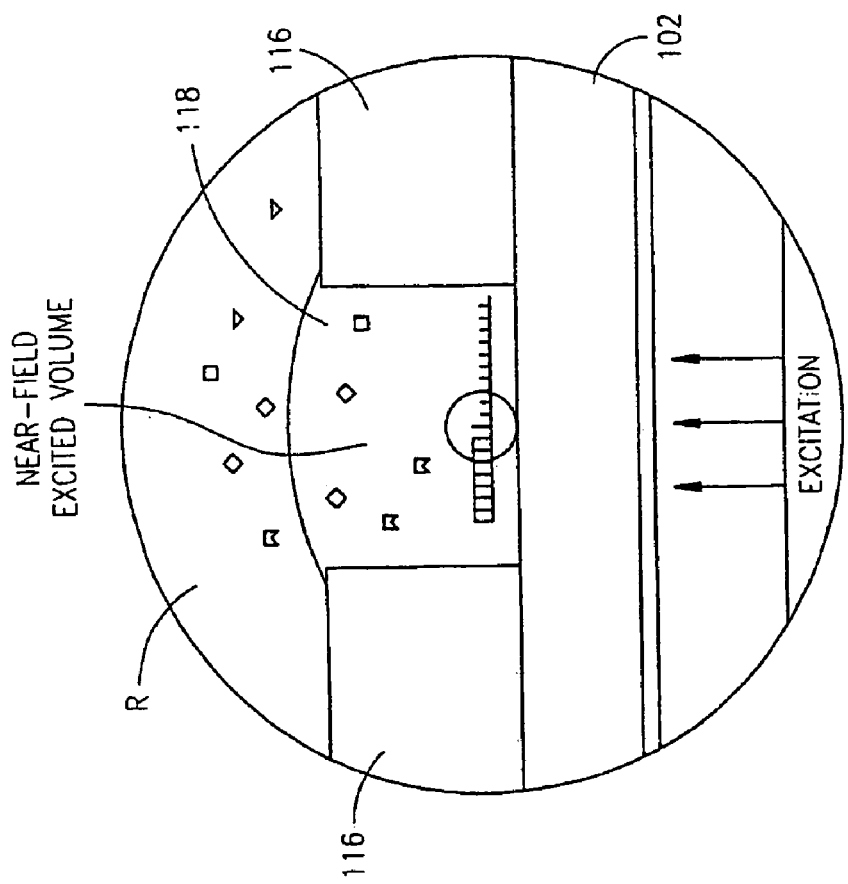
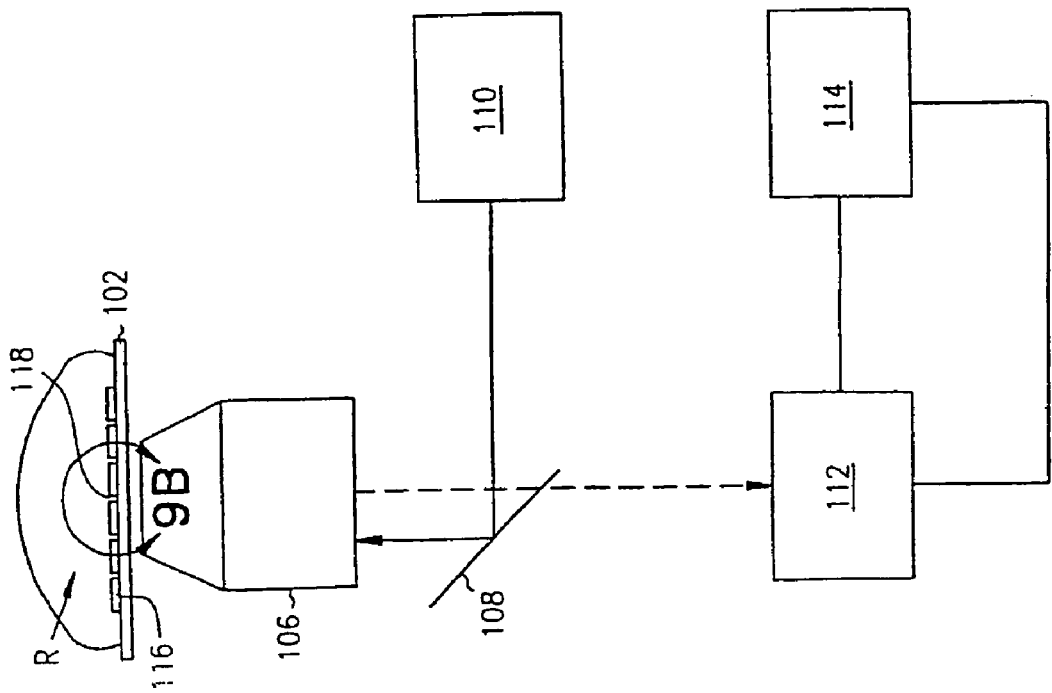

ZERO-MODE WAVEGUIDES

CROSS-REFERENCES

This application is a continuation application of Ser. No. 11/151,807, filed Jun. 13, 2005, now U.S. Pat. No. 7,013,054 which is a continuation application of Ser. No. 10/259,268, now U.S. Pat. No. 6,917,726, filed Sep. 27, 2002, which claims priority to U.S. Provisional Patent Application No. 60/325,280, filed Sep. 27, 2001, which is related to U.S. patent application Ser. No. 09/572,530, all of which are hereby incorporated by reference in their entirety.

This invention was made with funds provided by the U.S. Government under National Science Foundation Grant No. BIR8800278, and National Institutes of Health Grant No. P412RR04224-11, and Department of Energy Grant No. 066898-0003891. The U.S. Government may have certain rights in this invention.

FIELD OF THE INVENTION

The present invention is directed to zero-mode metal clad waveguides for performing spectroscopy with confined effective observation volumes.

BACKGROUND OF THE INVENTION

Observing and understanding the activity of a single molecule, such as an enzyme, is critical to understanding the dynamics of many important biochemical processes, such as catalysis, signal transduction, and gene regulation. Many biochemical reactions require micromolar ligand concentrations. In order to perform spectroscopy on one or a few molecules at such high concentrations, it is necessary to limit the size of the effective observation volume.

Previous attempts at sub-diffraction limited spectroscopy have included the utilization of near-field apertures. These implementations typically involve an optical fiber that has been tapered to a sub-wavelength point and coated with a metal such as aluminum. A subwavelength aperture is formed in the metal at the end of the fiber. Excitation light is sent down the fiber towards the aperture, and the elements to be studied are present outside the fiber and in close proximity to the aperture. The subwavelength nature of the aperture results in a light diffraction pattern that includes evanescent modes. These modes rapidly decay with distance from the aperture, thus effectively confining the volume of illumination. Only a very small percentage of light sent down the fiber makes it through the near-field aperture to the illumination region, making the prior art very inefficient.

Additionally, the spectroscopic signal from the analyte is best collected externally by an additional apparatus, such as a microscope objective, since the efficiency of collection by the near-field fiber is very low.

The present invention is directed to overcoming these deficiencies in the prior art.

SUMMARY OF THE INVENTION

The present invention is directed to a method for analysis of an analyte. The method involves providing a zero-mode waveguide which includes a cladding surrounding a core, where the cladding is configured to preclude propagation of electromagnetic energy of a frequency less than a cutoff frequency longitudinally through the core of the zero-mode waveguide. The analyte is positioned in the core of the zero-mode waveguide and is subjected, in the core of the zero-mode waveguide, to activating electromagnetic radiation of a frequency less than the cutoff frequency under conditions effective to permit analysis of the analyte in a volume that is more compact than if the analysis were carried out in the absence of the zero-mode waveguide.

The apparatus of the present invention is used for analysis of an analyte. This includes a zero-mode waveguide having a cladding surrounding a core, where the cladding is configured to preclude propagation of electromagnetic energy of a frequency less than a cutoff frequency longitudinally through the core of the zero-mode waveguide. In addition, this apparatus has a source of electromagnetic radiation positioned relative to the zero-mode waveguide to direct electromagnetic radiation of a frequency less than the cutoff frequency into the core under conditions effective to permit analysis of an analyte in an effective observation volume which is more compact than if the analysis were carried out in the absence of the zero-mode waveguide.

In one embodiment of the present invention, the apparatus includes a superstructure contacted with the opaque film that serves to facilitate the use of a single chip with several different samples to be analyzed. In this embodiment, the zero-mode waveguides are positioned in an array such that several identical devices are spaced at equal intervals across the surface of the chip. The superstructure serves to isolate each device on the chip from all of the rest, allowing an individual device on a chip to be used with a particular sample without contaminating the rest of the devices on the chip.

In another embodiment of the present invention, a different superstructure is applied to a chip containing an array of zero-mode waveguide devices to facilitate the delivery of a small, accurately metered quantity of sample to each device on the chip. In this embodiment the superstructure contains microfluidic channels positioned to allow sample introduced at one or more input ports to be delivered to fluid cavities positioned over each of the zero-mode waveguide devices. The microfluidic portions of the superstructure can be used simply to convey and measure the sample, or more sophisiticated operations such as capillary electrophoresis can be performed on the sample before it reaches the zero-mode-waveguide device for optical analysis.

BRIEF DESCRIPTION OF THE DRAWINGS

FIGS. 9A and 9B show a system utilizing a zero-mode waveguide in accordance with the present invention.

DETAILED DESCRIPTION OF THE INVENTION

The present invention is directed to a method for analysis of an analyte. The method involves providing a zero-mode waveguide which includes a cladding surrounding (i.e. partially or fully) a core, where the core is configured to preclude propagation of electromagnetic energy of a frequency less than a cutoff frequency longitudinally through the zero-mode waveguide. The cutoff frequency is defined as the frequency below which the waveguide is incapable of propagating electromagnetic energy along the waveguide under the illumination geometry used. In one embodiment, the core is sufficiently small to preclude the propagation of electromagnetic energy of frequency below the cutoff frequency under any illumination geometry. A further embodiment uses a waveguide that is capable of supporting one or more longitudinally propagation modes of electromagnetic energy. In this embodiment, a special illumination geometry is used such that minimal or no energy is coupled into the propagating modes of the waveguide. The analyte is positioned in the core of the zero-mode waveguide and is subjected, in the core of the zero-mode waveguide, to activating electromagnetic radiation of a frequency less than the cutoff frequency under conditions effective to permit analysis of the analyte in an effective volume which is more compact than if the analysis were carried out in the absence of the zero-mode waveguide.

The apparatus of the present invention is used for analysis of an analyte. This includes a zero-mode waveguide having a cladding surrounding a core, where the core is configured to preclude propagation of electromagnetic energy of a frequency less than a cutoff frequency longitudinally through the zero-mode waveguide. In addition, this apparatus has a source of electromagnetic radiation positioned relative to the zero-mode waveguide to direct electromagnetic radiation of a frequency less than the cutoff frequency into the core under conditions effective to permit analysis of an analyte in an effective observation volume which is more compact than if the analysis were carried out in the absence of the zero-mode waveguide.

Figure 1:
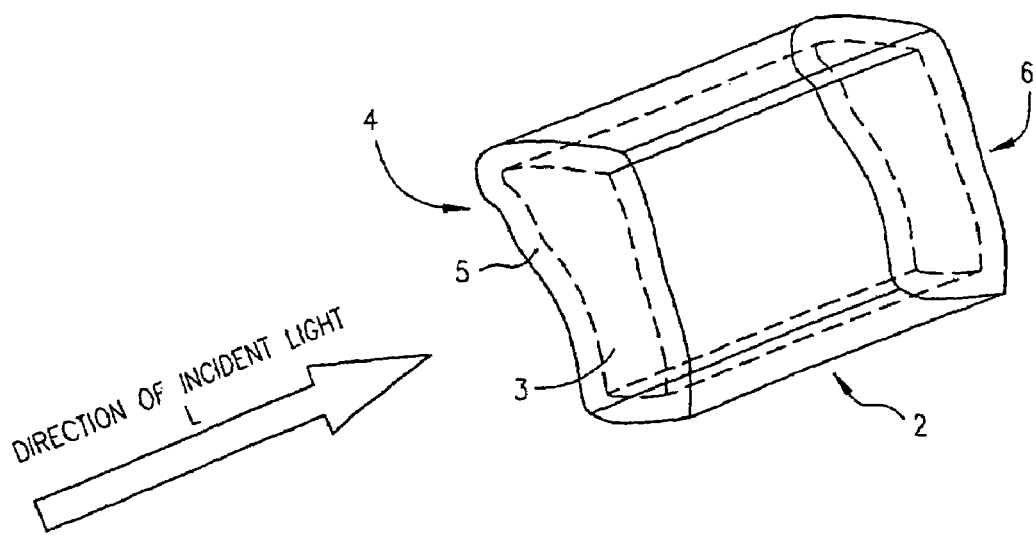
FIG. 1 is a perspective view of a metal-clad zero-mode waveguide with lateral dimensions, d, less than half the wavelength of illuminating light, in accordance with the present invention.

The present invention relates to zero-mode waveguides and their use to confine the effective observation volumes that are smaller than the normal diffraction limit. As shown in FIG. 1, excitation radiation (e.g., incident light) L enters waveguide 2, having core 3 and cladding 5, at entrance pupil 4. The waveguide comprises an internal volume with lateral dimensions (d) smaller than half the wavelength ($\lambda$) of the excitation light. This internal volume (i.e. the core) is comprised of a material that includes, or is capable of including, one or more elements of the material on which one or more forms of spectroscopy are to be performed. The volume external to the internal volume in the lateral directions is the cladding which is composed of a metal or metal-like material. The end of the waveguide opposite entrance pupil 4 is the exit pupil 6. The excitation power within the waveguide decays along the length of the guide. The waveguide is long enough so that the observation volume is predominantly confined to the region internal to the waveguide. As a result, signal collected from extraneous elements is greatly reduced.

Figure 2:
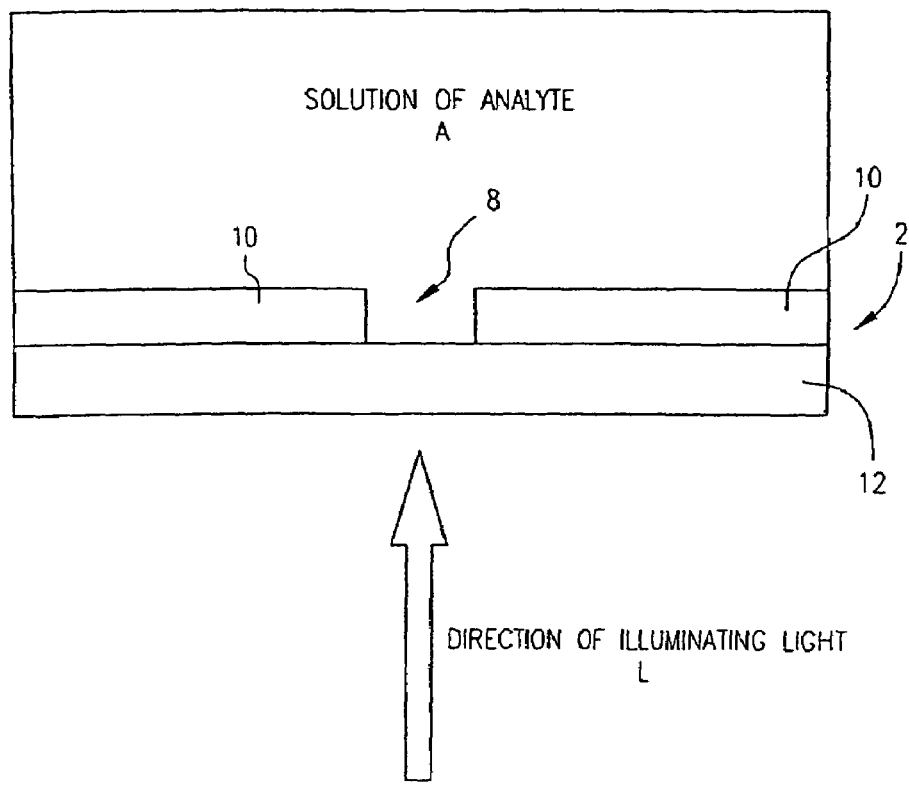
FIG. 2 is a cross-sectional view of one embodiment of a zero-mode waveguide in accordance with the present invention.

FIG. 2 is a cross-sectional view of one embodiment of a zero-mode waveguide in accordance with the present invention. This waveguide 2 is comprised of holes 8, which function as the core, in metal film 10, which functions as the cladding surrounding the core, on glass substrate 12. A solution of analyte is placed above and inside the waveguides. Illumination L is from below the zero-mode waveguide, and the spectroscopic signal from the analyte is detected through the glass substrate. The waveguide of FIG. 2 is preferably prepared by providing a glass or fused silica cover slip with an aluminum film on it. Chromium and other metals with small skin depth at the frequency of illumination used are also suitable for use in the zero-mode waveguide of the present invention. Holes 8 can be formed in the film by electron beam lithography. See Example 1, infra.

Other embodiments of the zero-mode waveguide of the present invention can be made by a number of techniques.

Figure 3A:
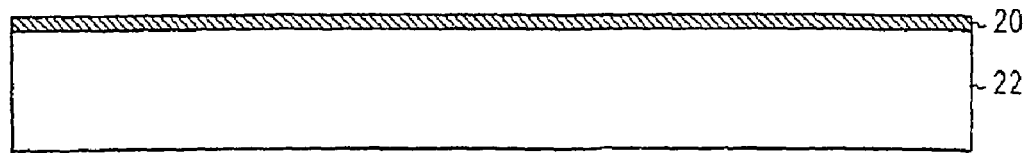
FIGS. 3A, 3B, 3C and 3D are a series of cross-sectional views, depicting one embodiment for the preparation of a zero-mode waveguide in accordance with the present invention.
Figure 3B:
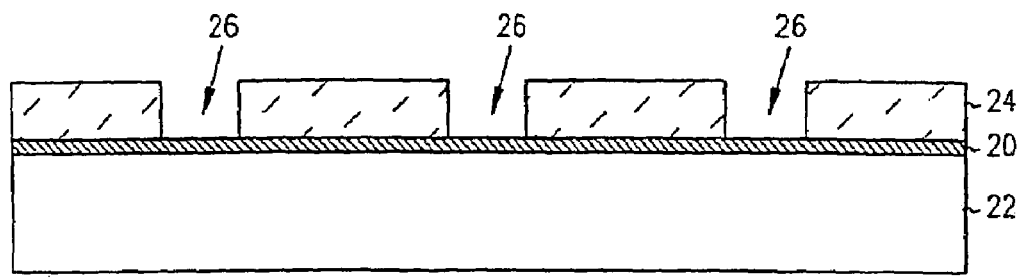
Figure 3C:
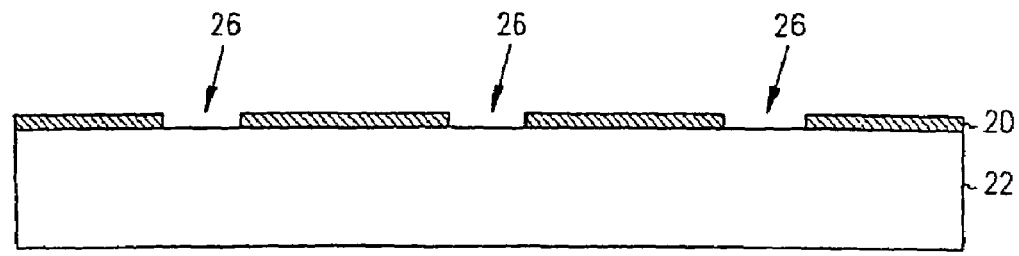
Figure 3D:
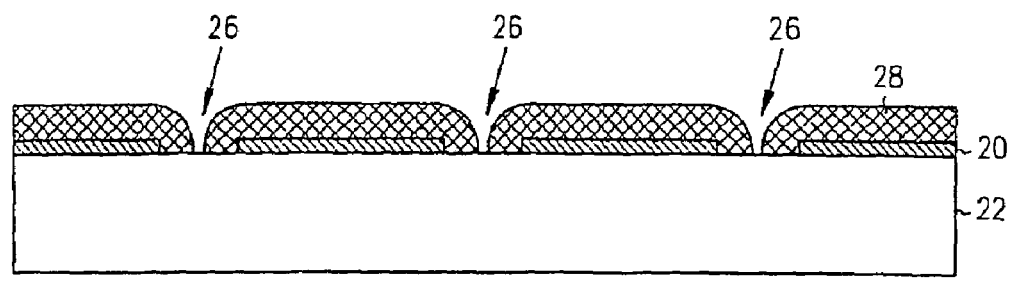

In another embodiment, as shown in FIGS. 3A, B, C and D, electroplating is used to progressively restrict larger holes in metal patterned using a low resolution patterning technique, such as photolithography. Electroplating will plate new metal only on those areas already metalized, so it will not deposit metal on the bare floors of the holes. However, it will deposit on the inside edges of the holes, so the holes will grow smaller in diameter as the film grows thicker. By choosing the appropriate time to discontinue deposition, the holes can be made sufficiently small to act as zero-mode waveguides. To fabricate these structures, a film of an appropriate priming metal 20, such as gold, is deposited on transparent (e.g., glass) substrate 22 (FIG. 3A). A layer of photoresist is then applied over the layer of priming metal (FIG. 3B). A cost-effective lower-resolution lithography system, such as 248 nm optical lithography, commonly known to practitioners in the art of optical lithography, produces holes in a photoresist mask layer 24 as small as 150 nm in diameter (FIG. 3B). This pattern of holes 26 is then transferred from layer 24 to the metal priming layer 20 (FIG. 3C) by wet etching, reactive ion etching, or ion milling—all techniques commonly known in the art. After removal of excess resist, a cladding material 28, such as chromium, is then electroplated onto priming layer 20 (FIG. 3D). The electroplating process will deposit cladding on the metal primed surfaces 20 but not the bare glass surfaces 22 located at holes 26. Because of this, the radius of the holes will shrink a distance equal to the thickness of the plated film. By appropriate selection of the plating time, or by optical feedback control, the holes can be constricted to much smaller dimensions. Holes as small as 1 nm can be consistently fabricated using related techniques. See Kang et al., "Investigations of Potential—Dependent Fluxes of Ionic Permeates in Gold Nanotubule Membranes Prepared Via the Template Method," *Langmuir* 17(9):2753–59 (2001) ("Kang"), which is hereby incorporated by reference. After electroplating, the device is ready for use.

Figure 4A:
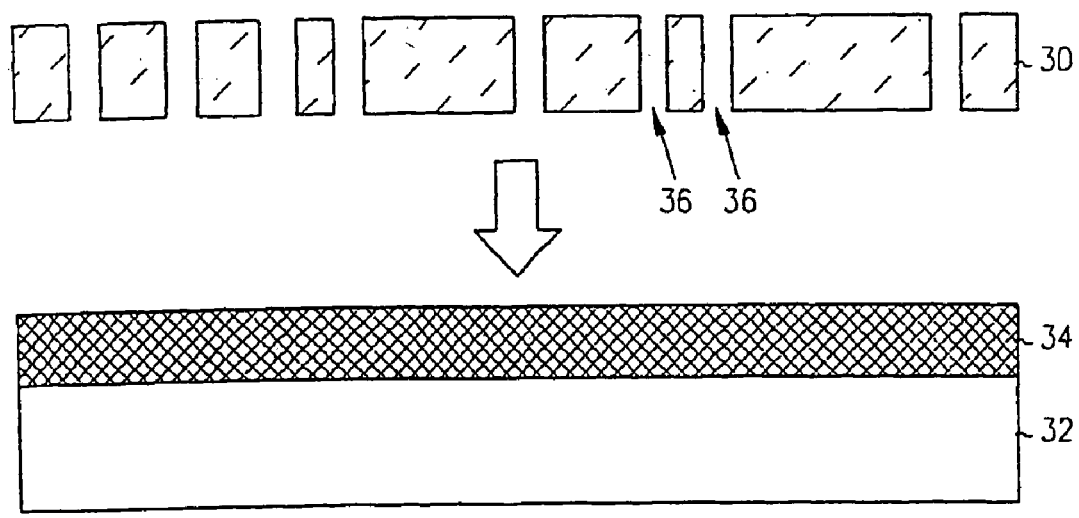
FIGS. 4A, 4B, and 4C are a series of cross-sectional views, depicting another embodiment for the preparation of a zero-mode waveguide in accordance with the present invention.
Figure 4B:
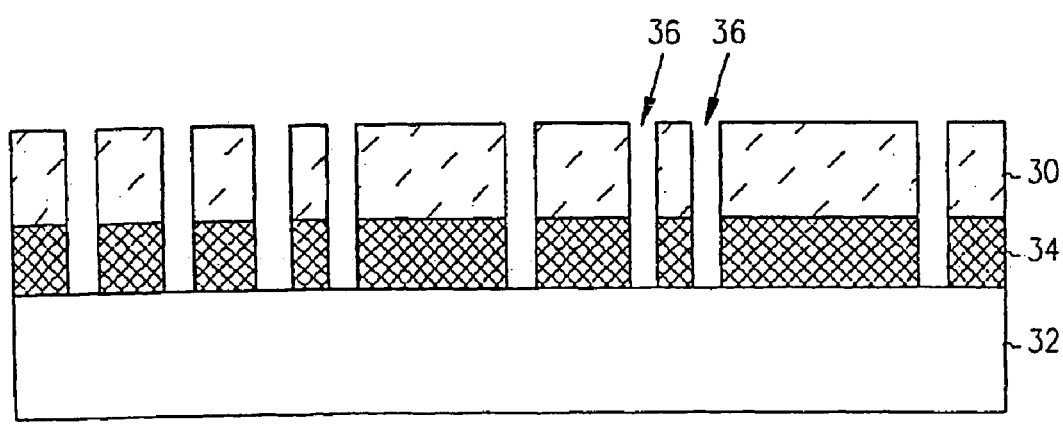
Figure 4C:
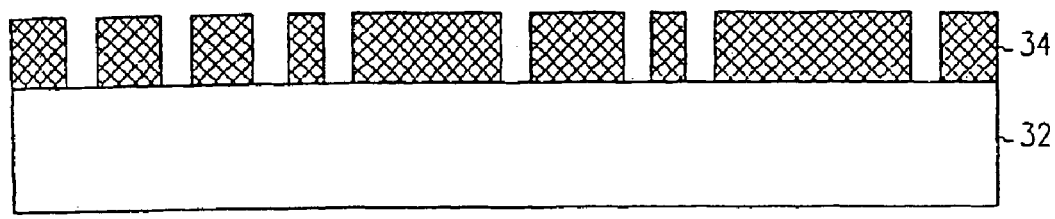

In another embodiment for preparation of zero-mode waveguides in accordance with the present invention, as shown in FIGS. 4A, B and C, a membrane filter (commercially available under trade names, such as NUCLEOPORE membranes (Whatman, Clifton, N.J.), and TRACK ETCH membranes (Whatman, Clifton, N.J.)) is used in place of an electron beam resist as the etch mask. In techniques commonly known in the art of filter fabrication, free-standing films of polymer (usually polycarbonate) are subjected to bombardment by energetic ionized nuclei, generated by either a Van De Graff generator or a nuclear reactor. These fragments penetrate the entire thickness of the membrane and cause chemical changes to the polymer in the vicinity of the trajectory of the energetic nucleus. These chemical changes induce a difference in solubility of the polymer in an etchant, commonly potassium hydroxide. The films are bathed for some duration in the etchant, causing the film to dissolve in the vicinity of the nuclear trajectories in the membrane. These holes can be quite small (as small as 15 nm) and quite consistent in size (i.e., the variability is less than 4 nm). Film 30 fabricated in this manner is directly applied to thin metal film 34 which is deposited on transparent substrate 32 (FIG. 4A). The pattern of pores 36 in polymer film 30 is then transferred to the metal film by any of a number of techniques (FIG. 4B), including reactive ion etching, wet chemical etching, and ion milling. The remaining polymer film 30 is then removed (FIG. 4C) with a solvent suitable to dissolve the polymer (such as toluene or xylenes in the case of polycarbonate) or an oxygen plasma clean process (known to those in the art of plasma processing).

Figure 5A:
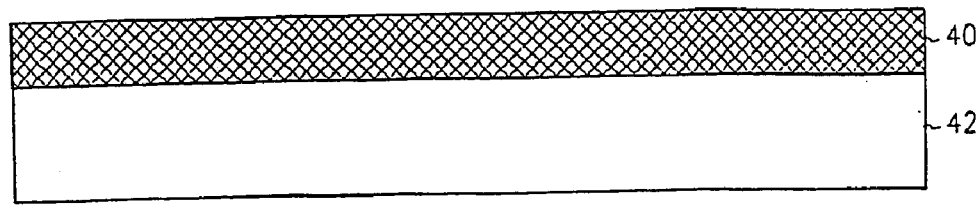
FIGS. 5A, 5B, 5C, 5D and 5E are a series of cross-sectional views, depicting a further embodiment for the preparation of a zero-mode waveguide in accordance with the present invention.
Figure 5B:
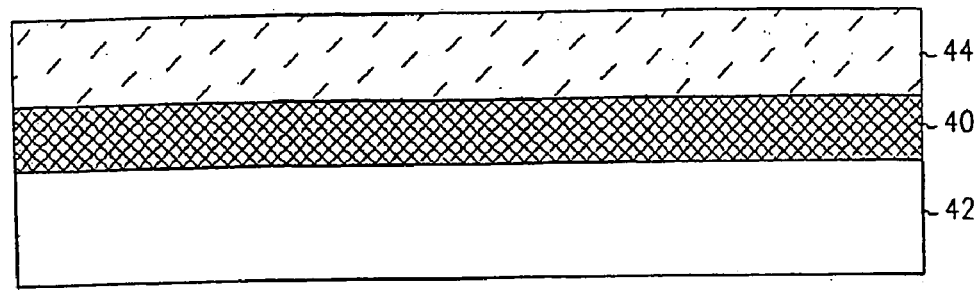
Figure 5C:
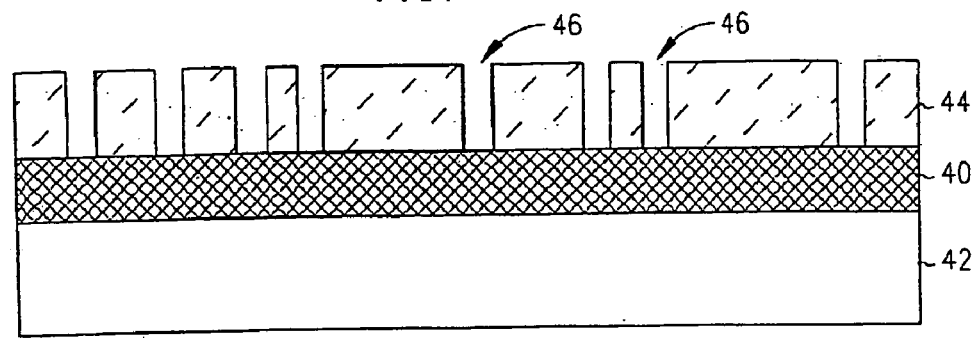
Figure 5D:
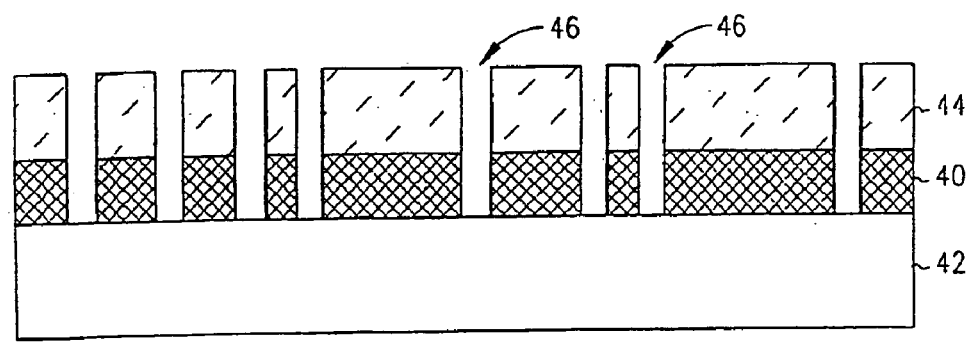
Figure 5E:
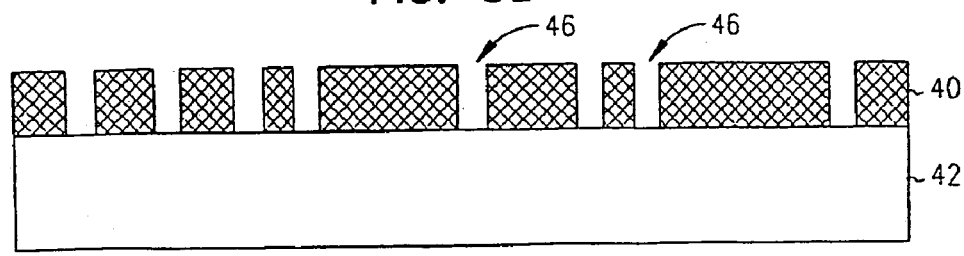

In another embodiment for preparation of zero-mode waveguides in accordance with the present invention, as shown in FIGS. 5A, B, C, D and E, a thin film of a suitable polymer material is deposited on a metal film and exposed to bombardment by high-energy ions and etched in a manner very similar to the etching techniques discussed above. In this embodiment, cladding material (e.g., chromium, aluminum, or gold) 40 is evaporated onto transparent (e.g. glass) substrate 42 (FIG. 5A) and thin polymer film 44 is spin-cast (FIG. 5B) directly onto the metal surface (as opposed to a free-standing membrane as in the embodiment of FIGS. 4A–C). The entire substrate with the metal and polymer film is then subjected to ion bombardment, as in the embodiment of FIGS. 4A–C, and the polymer film is developed with a solvent which will dissolve zones near the trajectory of an energetic nucleus (FIG. 5C), but not the unaltered film. The pattern of holes 46 which is thus created in the thin film of polymer 44 is then transferred into metal layer 42 using reactive ion etching, wet chemical etching, or ion milling (FIG. 5D). After pattern transfer, the remains of the polymer film are removed (as above) with a suitable stripping solvent or an oxygen plasma (FIG. 5E).

Figure 6A:
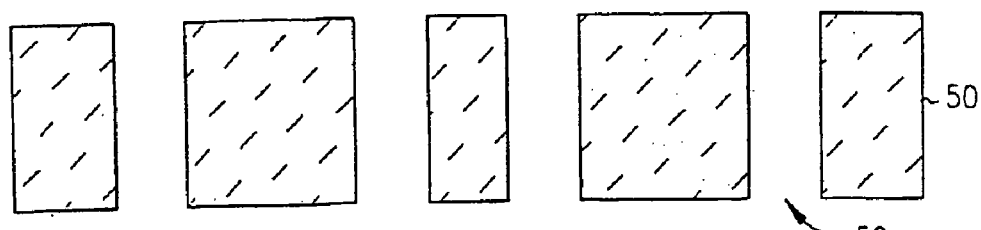
FIGS. 6A, 6B, 6C and 6D are a series of cross-sectional views, depicting another embodiment for the preparation of a zero-mode waveguide in accordance with the present invention.
Figure 6B:
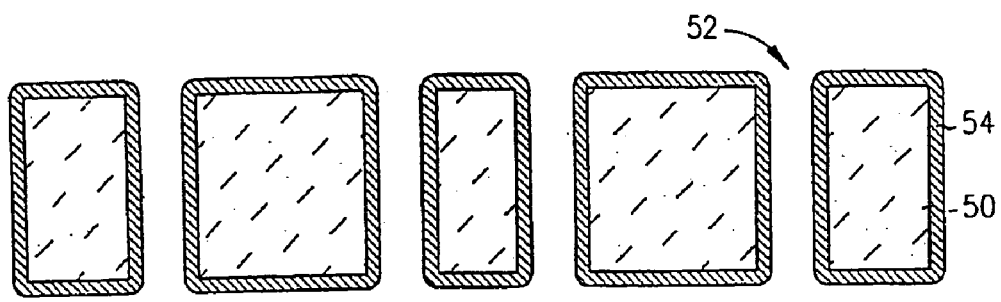
Figure 6C:
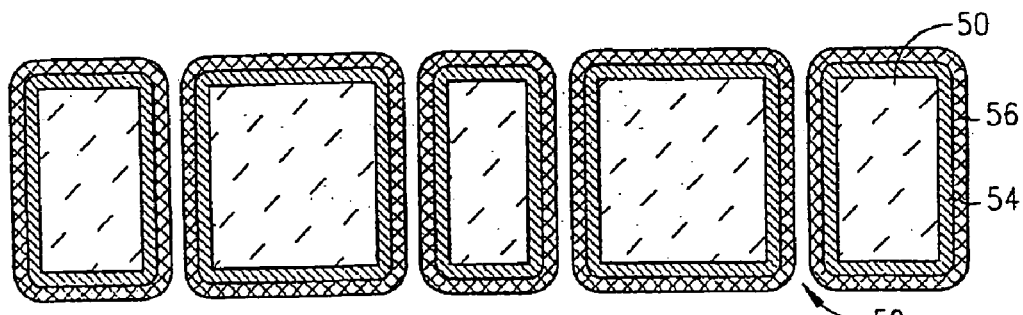
Figure 6D:
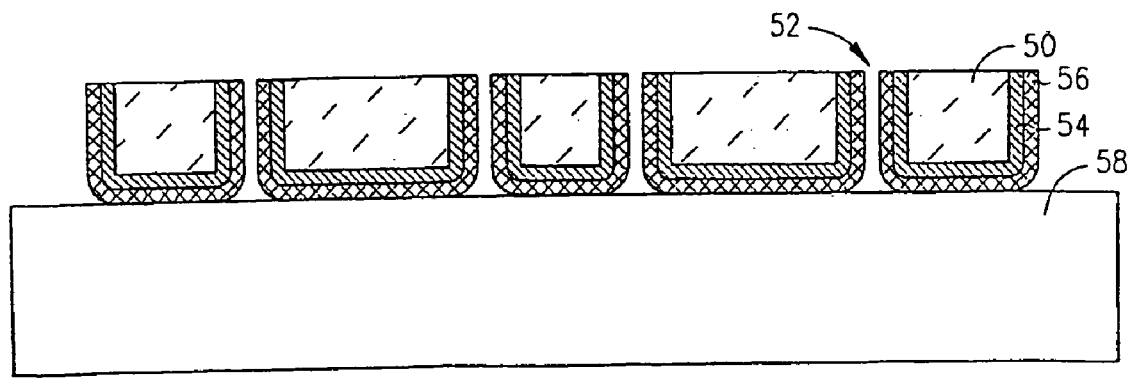

In another embodiment for preparation of zero-mode waveguides in accordance with the present invention, as shown in FIGS. 6A, B, C and D, the zero-mode waveguides are fabricated directly in etched membrane 50 (FIG. 6A). Following the methods of Kang, a layer of gold 54 is deposited on all surfaces of a polycarbonate film, including the cylindrical interiors of pores 52 (FIG. 6B). This gold film is used as a priming layer to electroplate a cladding layer material 56, such as chromium (FIG. 6C). The membrane filters are commercially available with pores in a wide variety of dimensions. In one embodiment, 100 nm pores are primed with 5 nm of gold and then plated with 30 nm of chromium, leaving a 30 nm interior waveguide core with a 30 nm cladding layer of chromium. These structures can be optionally immobilized on a transparent (e.g. glass) substrate 58 and optionally thinned by any of the material removal techniques well-known to those in the art of thin film processing (FIG. 6D).

Figure 7A:
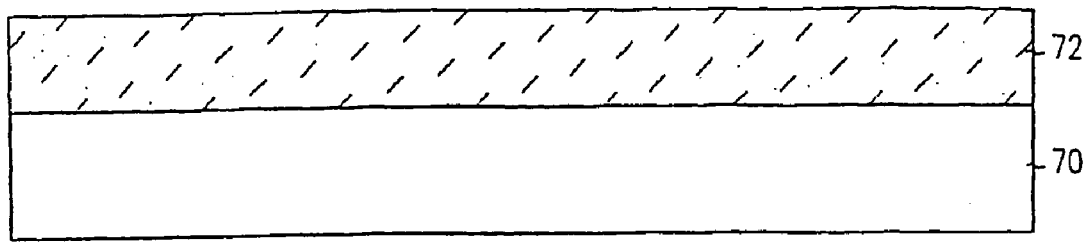
FIGS. 7A, 7B, 7C and 7D are a series of cross-sectional views, depicting a further embodiment for the preparation of a zero-mode waveguide in accordance with the present invention.
Figure 7B:
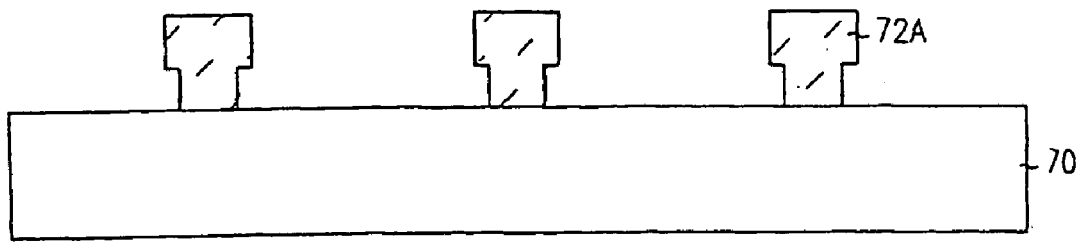
Figure 7C:
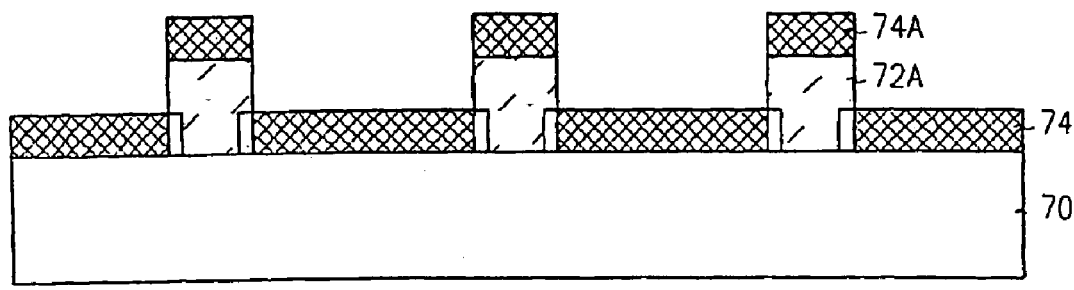
Figure 7D:
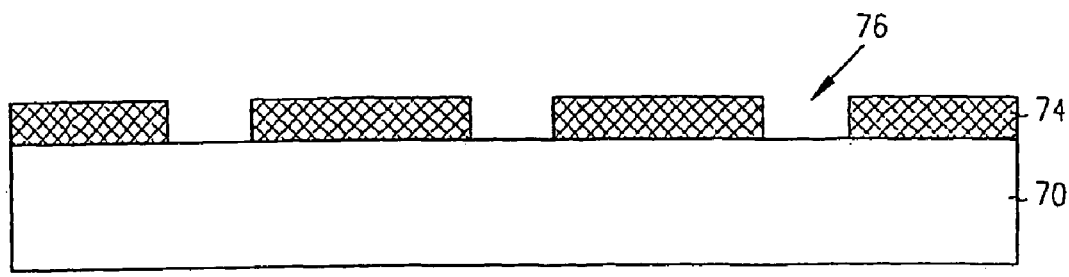

In another embodiment for the preparation of zero-mode waveguides in accordance with the present invention, as shown in FIGS. 7A, B, C and D, cladding material lift-off is carried out using an opposite tone film or pattern. This embodiment involves first applying polysilicon layer 72 over light transmitting (e.g., fused silica) substrate 70, as shown in FIG. 7A. Polysilicon pillars 72A are then formed from polysilicon layer 72 using conventional photolithography, as shown in FIG. 7B. Pillars 72A are reduced in size by baking in an oxygen atmosphere followed by treatment with an etchant, such as hydrofluoric acid. As shown in FIG. 7C, substrate 70 and pillars 72A are then electroplated with metal layer 74 and 74A, respectively. Gold is a suitable metal layer for such purposes. Pillars 72A and metal 5 layer 74A are then removed by conventional techniques, leaving behind metal layer 74 with holes 76 over substrate 70, as shown in FIG. 7D.

Figure 8A:
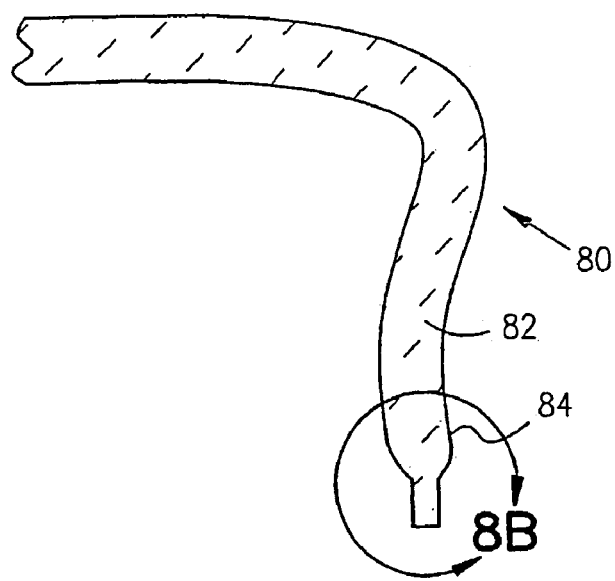
FIGS. 8A and 8B show an alternative embodiment of a zero-mode waveguide in accordance with the present invention where the waveguide is formed from an optical fiber and an enlargement of the tip of the zero-mode waveguide.
Figure 8B:
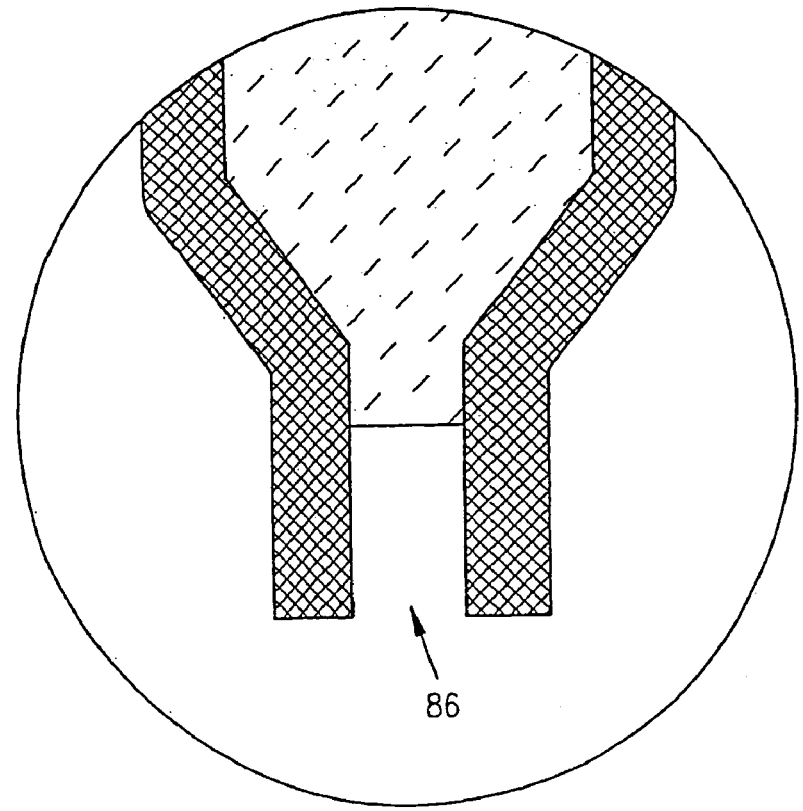

In another embodiment for preparation of zero-mode waveguides in accordance with the present invention, as shown in FIGS. 8A and B, a fiber tip 80, which is similar to a near-field scanning optical microscope tip is constructed so that it terminates with a zero-mode waveguide where the tip allows entrance of analyte material into the interior of the zero-mode waveguide. This embodiment of the present invention is prepared by heating the end of an optical waveguide fiber 82 and drawing it so that its diameter narrows at the heated end. The resulting tapered tip is coated with zero-mode cladding material 84. The silica of fiber 82 is then etched (e.g., with hydrofluoric acid) a small distance to form hole 86 which serves as the core for the zero-mode waveguide.

The use of zero-mode waveguides, in accordance with the present invention, to analyze analytes is shown in FIG. 9B.

Surface 102 with metallic layer 116 applied over surface 102 with small holes 118 etched into opaque layer 116 represents one embodiment of the present invention. When illuminated from below, the light cannot penetrate fully through the holes into reagent solution R, because the diameter of holes 118 is smaller than one half of the light's wavelength. As shown in FIG. 9B, the material undergoing spectroscopic analysis is positioned in hole 118 and is illuminated from below. Because the effective volume of observation is very small, signals due to extraneous material in the vicinity will be reduced.

The system for carrying out analysis of analytes in accordance with the present invention is shown in FIG. 9A. Illumination source 110 (e.g., a laser) directs excitation radiation by way of dichroic beam splitter 108 through lens 106 and surface 102 to the target material. This excites the material with the resulting emitted radiation passing back through surface 102 and lens 106. Dichroic beam splitter 108 allows passage of the emitted radiation to detector 112 which identifies the type of emission. The detected emission information is then directed to computer 114 where the material corresponding to the emission is identified and its identity stored. The radiation being emitted can be in the form of fluorescence, Raman scattered light, Hyper-Rayleigh scattered light, luminescence, Hyper-Raman scattered light, or phosphorescent light.

The zero-mode waveguide of the present invention can be used to analyze a variety of analytes. Amongst these are biomolecules, such as proteins and nucleic acids.

The zero-mode waveguide of the present invention can be used for sequencing nucleic acid molecules, as fully described in U.S. patent application Ser. No. 09/572,530, which is hereby incorporated by reference. This method involves providing a complex of a nucleic acid polymerizing enzyme and a target nucleic acid molecule oriented with respect to each other in a position suitable to add a nucleotide analog at an active site complementary to the target nucleic acid. A plurality of types of nucleotide analogs are provided proximate to the active site, where each type of nucleotide analog is complementary to a different nucleotide in the target nucleic acid, leaving the added nucleotide analog ready for subsequent addition of nucleotide analogs. The nucleotide analog added at the active site as a result of the polymerizing step is identified. The steps of providing a plurality of nucleotide analogs, polymerizing, and identifying are repeated so that the sequence of the target nucleic acid is determined. The zero-mode waveguide of the present invention is used to carry out the step of identifying the nucleotide analog added to the target nucleic acid.

The zero-mode waveguide of the present invention can also be used to analyze other enzymatic reactions, including haplotyping with DNA polymerase, enzymatic reactions with RNA polymerase or helicase/primase, and analysis of ribosomes, spliceosomes, transcription complexes, chaperon proteins, protein folding, virus particle assembly, catalytic or non-catalytic antibodies, ribozymes, proteins involved in nucleic acid recombination, exonucleases, endonucleases, inorganic catalysts, and detection of viruses or other small pathogens.

The zero-mode waveguide of the present invention can be used to analyze one or more analytes, either sequentially or simultaneously within the waveguide.

EXAMPLES

Example 1

Fabrication of Zero-Mode Waveguide Array

Arrays of zero-mode waveguides were manufactured as small holes in a 50 nm thick film of aluminum on a glass or fused silica coverslip. The steps for the fabrication of the devices are as follows. First, the cover glasses were cleaned with a solution of one part ammonium hydroxide, one part hydrogen peroxide, and six parts water at 70° C. The coverglasses were immersed in this solution for 10 minutes, and then rinsed in a overflowing bath of deionized water for 10 minutes. The samples were dried with compressed dry nitrogen and then subjected to oxygen plasma for 3 minutes. The cleaned cover glasses were then coated with 50 nm of aluminum by thermal evaporation. An electron beam lithography resist, ZEP-7000A, was spun onto the cover glasses for 60 seconds at 3000 RPM. Excess solvent was driven from the films by baking on a temperature-controlled hotplate for 30 minutes at 170° C. This process yields a film approximately 300 nm thick. The films were then mounted for exposure in an electron-beam lithography system. Electron beam exposure was performed in a pattern of dots separated by 5 micrometers (for optical isolation during use). A range of doses can be used to generate a gradation of hole sizes on a single coverglass for studies where variable hole size is useful. The latent pattern was then developed using a solution of xylenes at room temperature for 3 minutes. The development was stopped with a rinse of isopropanol, followed immediately by drying with compressed dry nitrogen. The developed pattern was then transferred to the aluminum layer by reactive ion etching using an aluminum etch recipe: 20 sccm $Cl_2$, 40 sccm $BCl_3$, and 2 sccm $H_2$. The pressure was maintained at 20 mT, and the radio-frequency power was controlled by feedback to hold the sample bias potential at 400 V. The etch proceeded for approximately 1 minute and 20 seconds. Immediately after removal from the etch chamber, the samples were rinsed in deionized water to remove residual chlorine radicals which can degrade the structures on exposure to moisture in the air. The remaining resist was exposed to short-wavelength ultraviolet radiation to expose it, and the exposed resist was removed with another developer for this film: methyl isobutyl ketone ("MIBK"). Again, the samples were rinsed in isopropanol and blown dry with compressed dry nitrogen. The final step before use was to subject them to an oxygen plasma to harden the aluminum native oxide and remove any organic residue from processing. A total of 3 minutes of exposure at 1000 watts was used, but the radio-frequency power was turned off and on to keep the substrate temperature below 120° C. to prevent damage to the aluminum film.

Figure 10:
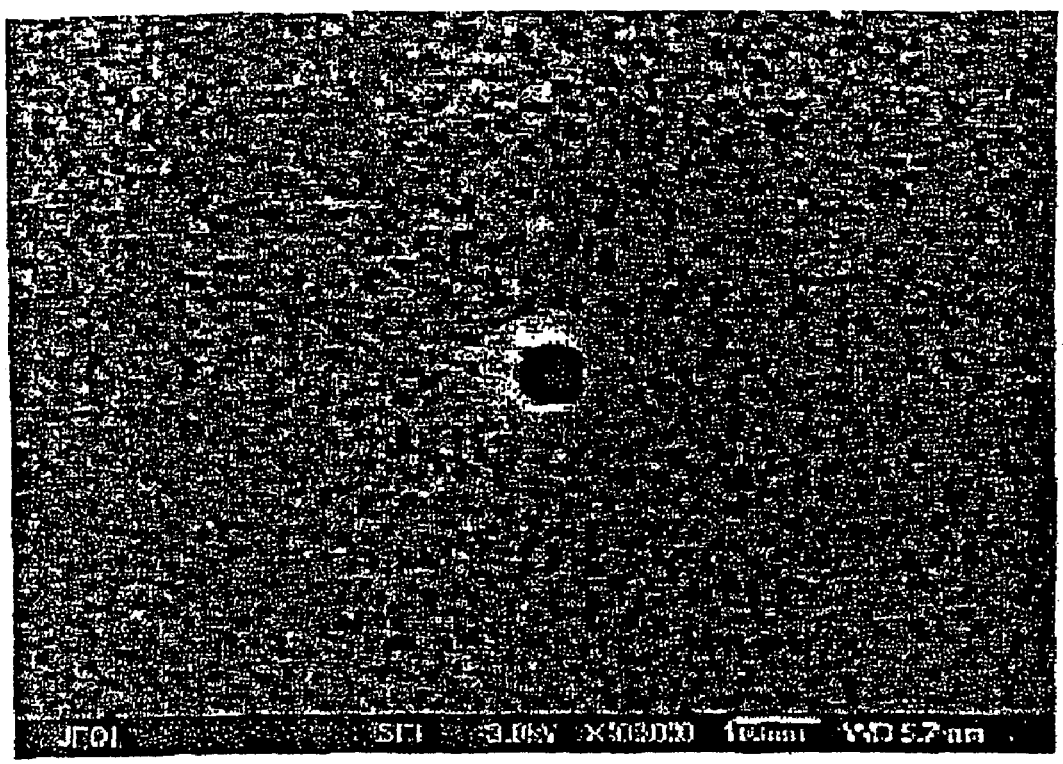
FIG. 10 is a scanning electron micrograph showing a top view of a zero-mode waveguide prepared in accordance with the present invention.

FIG. 10 is a scanning electron micrograph showing a top view of the zero-mode waveguide made by the process of this example.

Example 2

Intensity Evaluation with Zero-Mode Waveguide Array

Simulations of the electric field inside zero-mode waveguides were performed using a commercial finite-element time-domain Maxwell's equation solver (EMFlex, from Weidlinger Associates, New York, N.Y.). Models were run for right, circular cylindrical waveguides of water in 50 mm thick aluminum films on a glass substrate (index of refraction 1.5). The entire region above the aluminum and inside the waveguides was assumed to be filled with water, and the illumination was, in all cases, normally incident circularly polarized plane waves of light at $6 \times 10^{14}$ Hz (corresponding to a vacuum wavelength of 500 mm). The entire region of the model was 1 µm³, and the grid spacing inside and in the vicinity of the waveguides was 1 nm. Although actual experiments would in most cases use tightly focused light, rather than the plane waves modeled here, the dimensions of the waveguides modeled are small enough compared with the wavelength of light to make the plane wave approximation accurate enough to estimate the intensity distribution within the waveguides. Models were run for waveguide diameters between 30 and 100 nm.

Figure 11:
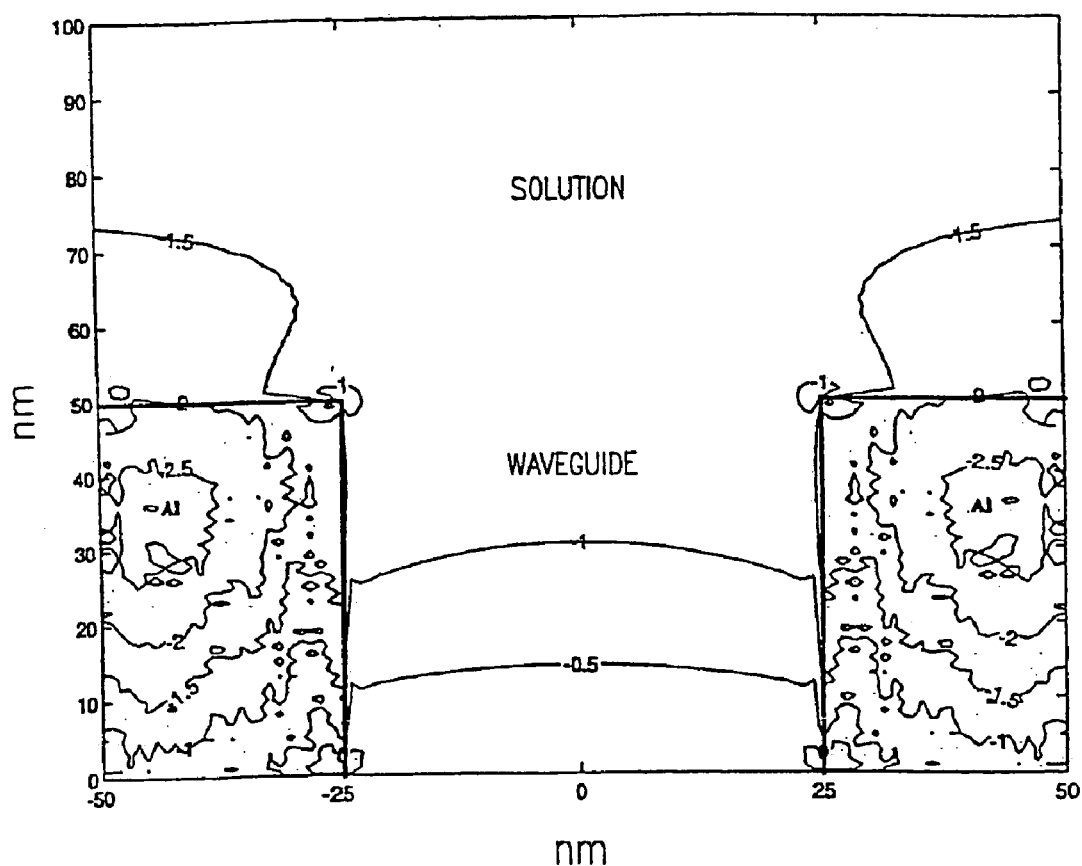
FIG. 11 is a contour plot of the logarithm of the intensity distribution in a 50 nm diameter cylindrical waveguide viewed from the side at the diameter. The heavy lines mark the borders of the waveguide, and the calculation is for 500 nm light in a water-filled, aluminum-clad waveguide.
Figure 12:
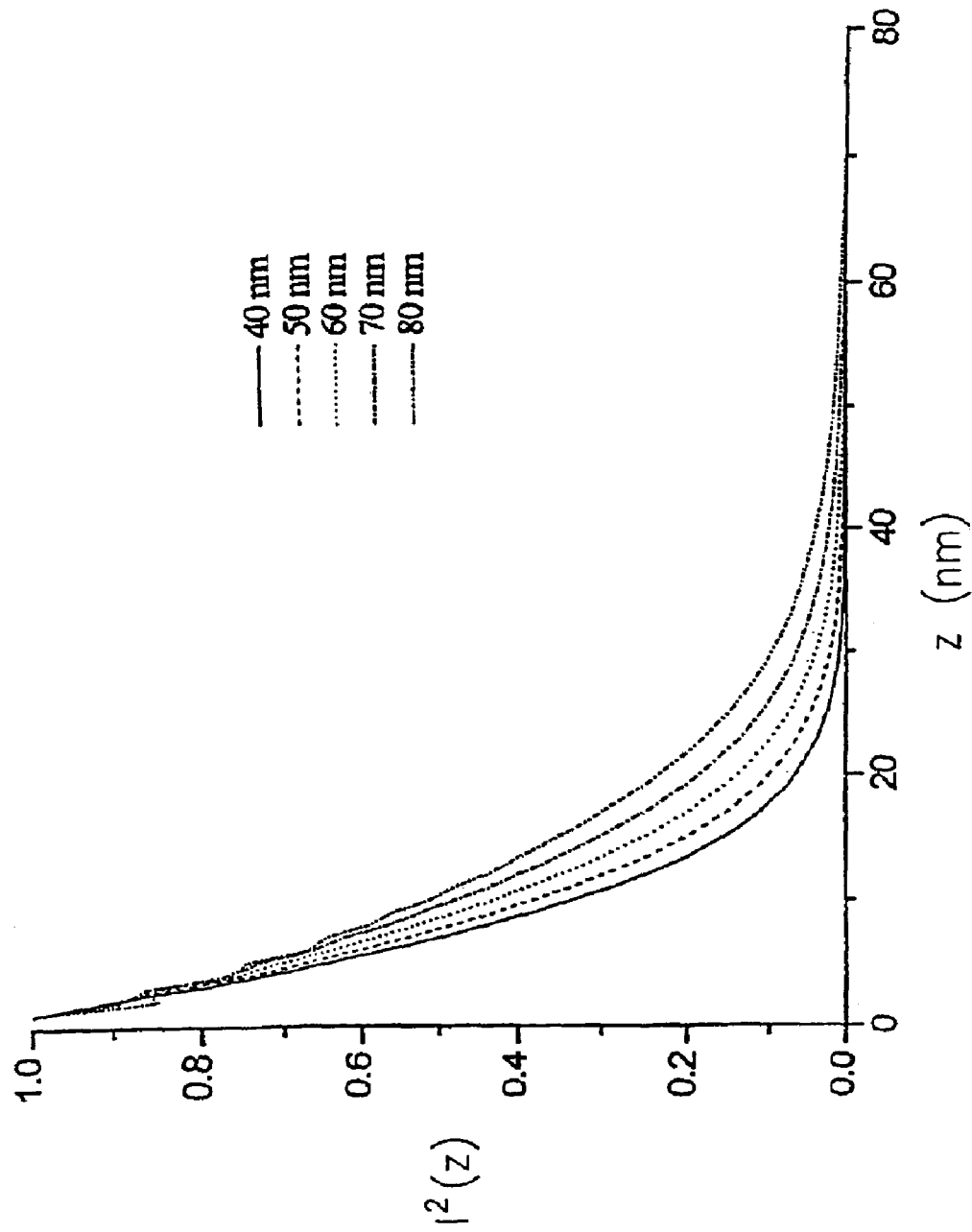
FIG. 12 is a graph of the intensity squared as a function of depth into cylindrical waveguides of various diameters for 500 nm light.

FIG. 11 shows the calculated intensity distribution for a 50 nm diameter waveguide. The intensity falls off quickly with increasing propagation into the waveguide, as expected for light that is well below the cut-off frequency for the guide. The intensity distribution is relatively constant across the waveguide, as demonstrated in FIG. 11, and, therefore, one can estimate the effective illumination volume by plotting the intensity as a function of propagation distance. The ability of fluorescent photons to couple out of the waveguide will also be a strong function of distance from the entrance/exit pupil. This effect has been assumed to follow a behavior that is similar to that of the excitation light propagation. However, this assumption fails to take into account the orientation of the emitting dipole, its exact lateral location within the guide, or the different frequency of the emitted light. The effective observation volume is described by the illumination profile multiplied by the collection efficiency profile. The effective observation volume within a guide can, therefore, be approximated by the square of the intensity distribution. FIG. 12 shows the intensity squared as a function of propagation distance for guides of various diameters decreases. As expected, the intensity decays faster as the waveguide diameter decreases. Therefore, small diameter waveguides serve to decrease the effective observation volume both by physically constraining the experiment in the lateral dimensions and by decreasing the propagation distance of light into and out of the guide.

Example 3

Spectroscopy with Zero-Mode Waveguides

Figure 13:
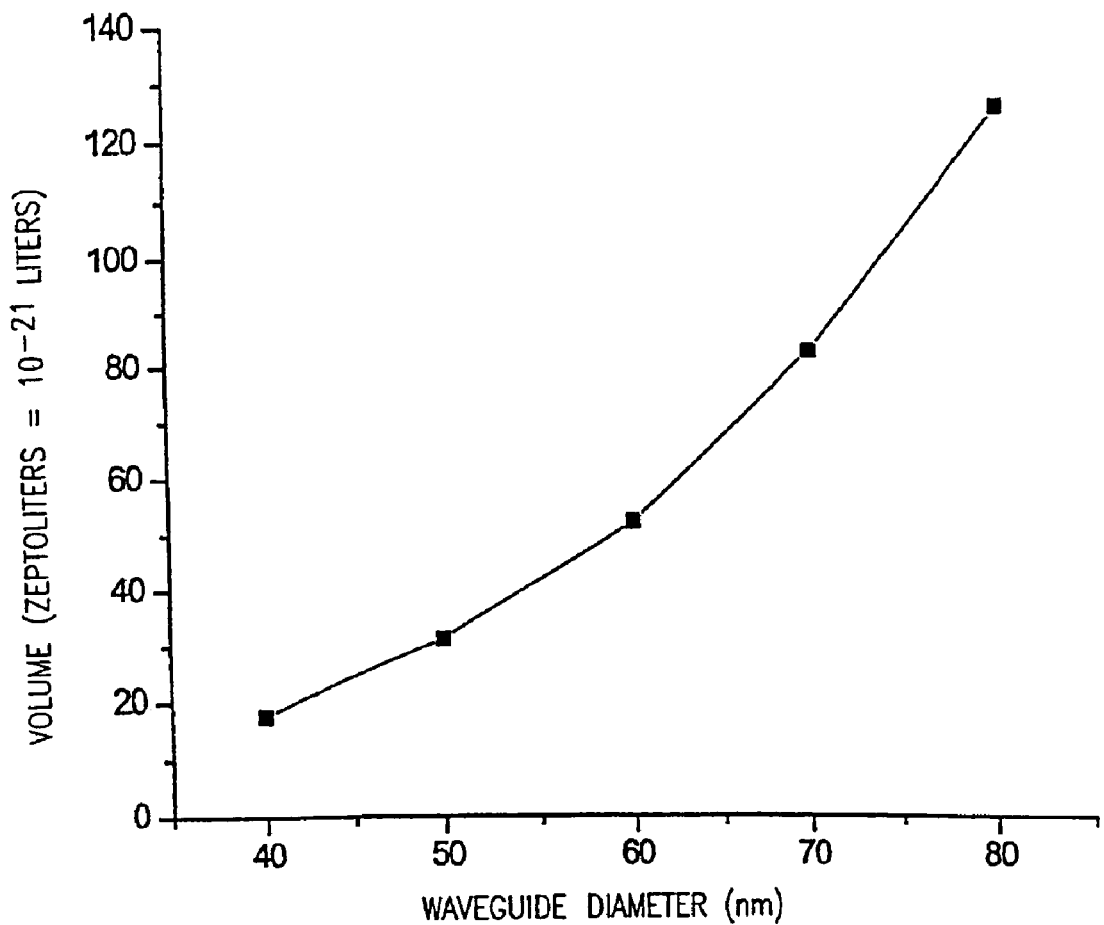
FIG. 13 is a graph of the effective observation volume in cylindrical waveguides as a function of waveguide diameter for 500 nm light.

For fluorescence applications, one can define the size of effective observation volume, V, as $$V = \frac{\int S(r) d^3 r \int S(r) d^3 r}{\int S^2(r) d^3 r}$$

where S(r) is the observation efficiency at the point r, and for this system $S(r) = I^2(r)$. FIG. 13 shows the effective volume of zero order waveguides in aluminum illuminated with $6 \times 10^{14}$ Hz light as a function of waveguide diameter. Volumes are on the order of 50 zeptoliters ($10^{-21}$ liters). This compares to 0.5 femtoliters ($10^{-15}$) for a typical diffraction-limited focal volume.

The effectiveness of the waveguides in confining the volume of illumination was evaluated using fluorescence correlation spectroscopy ("FCS"). FCS involves illumination of a sample volume containing dye molecules in solution. The diffusion of molecules into and out of the effective observation volume leads to fluctuations in the number of observed molecules and hence to fluctuations in the fluorescence signal. These fluctuations occur on a time scale that is characterized by an average residence time of a molecule within the volume, $\tau_D$. The autocorrelation of the fluorescence signal, $G(\tau)$, is given by $$G_{(\tau)} = \frac{\langle \delta F(t) \delta F(t+\tau) \rangle}{\langle F(t) \rangle^2},$$

where F(t) is the fluorescence signal at time t and $\delta F(t)$ is the deviation in fluorescence from the mean. G(0) is inversely proportional to the average number of molecules in the volume and the half-max of $G(\tau)$ occurs at the typical residence time of molecules diffusing in the volume. For a known concentration of dye in solution, the average number of molecules observed gives a useful estimate of the effective observation volume and is critical for determining the expected background from freely diffusing species in studies of single enzyme molecules in the presence of fluorescent ligands. The average residence time of diffusing dye molecules, and the overall shape of $G(\tau)$, can be combined with theoretical calculations to give an understanding of the shape of the effective observation volume. The residence time is also relevant to the temporal resolution of studies of enzymatic dynamics. Reactions that produce fluorescent product or intermediates may be distinguishable from background fluorescence fluctuations if the relevant reaction rates are longer than the typical diffusion time.

Arrays of waveguides were illuminated from the glass side with 488 nm circularly polarized light from an argon ion laser using a 60× water immersion microscope objective (UPlanApo Olympus, Melville, N.Y., NA=1.2). Fluorescence was collected by the same objective, passed through a dichroic mirror (dichroic long-pass 500, Chroma Technology Corp., Brattleboro, Vt.) and two emission filters (575/150 and 580/150) to block reflected laser light and coupled into a 50 µm optical fiber (OZ Optics Ltd., Corp., Ontario, Canada). A 50/50 fiber splitter was used to send the signal to two avalanche photodiodes ("APD"s) (Perkin Elmer Optoelectronics, Fremont, Calif.) for cross-correlation. Cross-correlation was necessary to remove artifacts from after-pulsing at short times in individual APDs. Cross-correlation is similar to auto-correlation and yields the same information, except that $G(\tau)$ is now given by $$G_{(\tau)} = \frac{\langle \delta F_1(t) \delta F_2(t+\tau) \rangle}{\langle F_1(t) \rangle \langle F_2(t) \rangle}$$

where subscripts indicate signals measured at different APDs.

Figure 14:
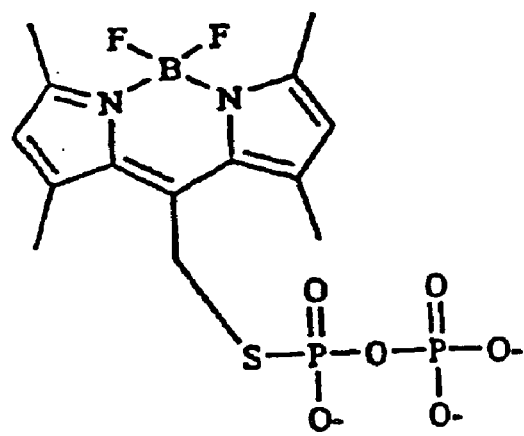
FIG. 14 is a drawing of the chemical structure of the dye BODIPY 515 pyrophosphate (Molecular Probes, Eugene, Oreg.).

Waveguide arrays were exposed to oxygen plasma for one minute and were pre-treated with a solution of heparin (50 µg/ml) in HPLC grade water on the aluminum side to prevent sticking of dye to the glass and metal surfaces. FCS was then performed on arrays with a 1 µM solution of the dye Bodipy 515 pyrophosphate (see FIG. 14) in HPLC grade water with 50 µg/ml of heparin. Molecules can diffuse into and out of the waveguide only through the top of the waveguide and the gradient of light intensity inside the waveguide is essentially one dimensional, as discussed above. Therefore, one would expect G(τ) to be dominated by the decay in 5 illumination intensity and fluorescence output coupling efficiency with increasing distance from the entrance pupil, both of which decay faster in smaller diameter waveguides.

Figure 15:
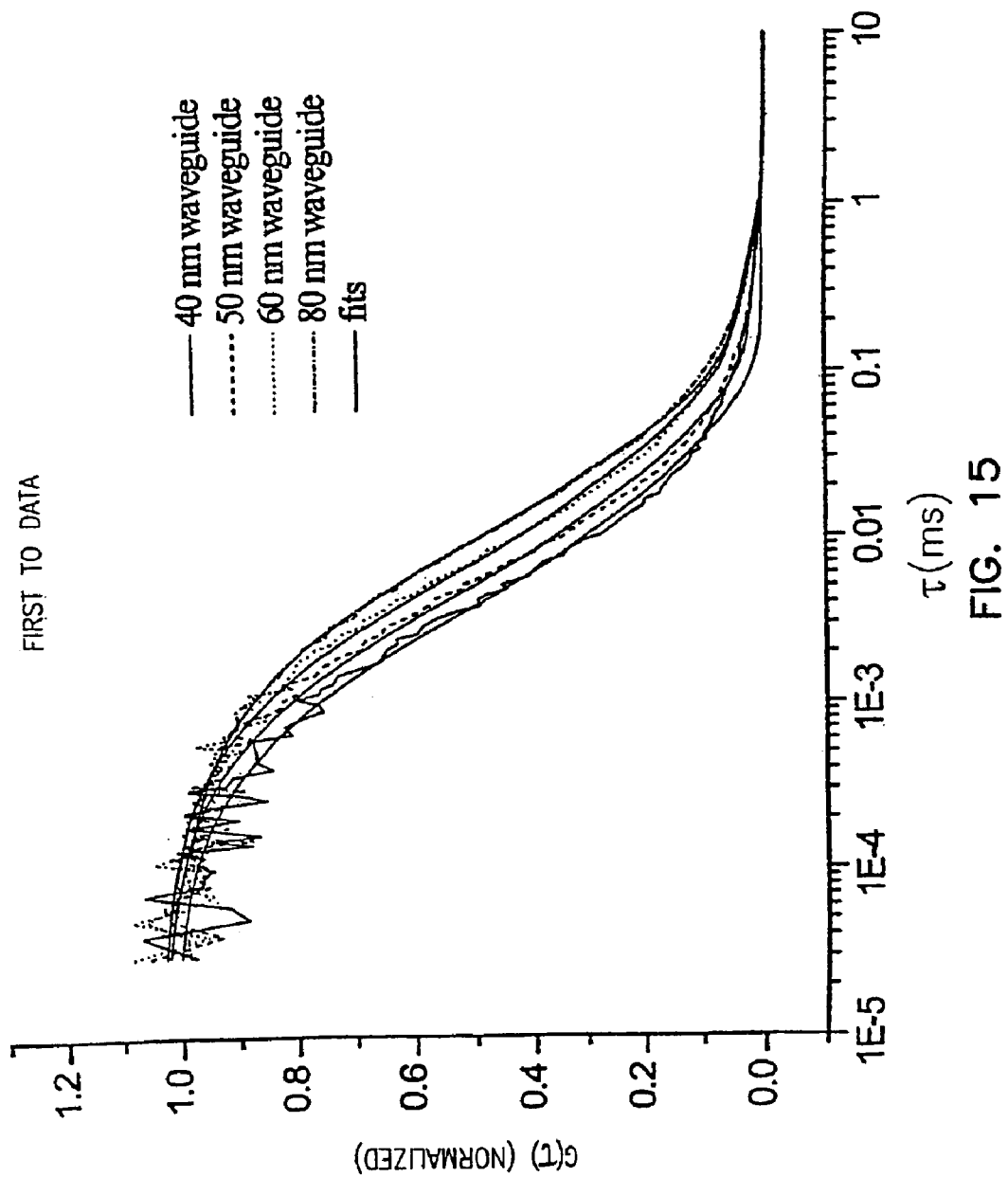
FIG. 15 is a graph fitting fluctuation correlation spectroscopy model to data for waveguides of various diameters.

Using the output from the finite-element simulations, theoretical FCS curves were generated for waveguides of various diameters and fit to the normalized data curves. Despite the use of heparin and oxygen-plasma treatment, the FCS curves displayed long-time tails attributable to some sticking of dye. This was accommodated for in the fitting function using an additive exponential term such that the fitting function was of the form $$G_{(\tau)} = \frac{1}{N} G_{\text{diff}}(\tau) + Se^{\frac{-t}{\tau_s}} + \text{offset}$$

where $G_{\text{diff}}$ is the numerically-derived diffusion component, S and $\tau_s$ are the sticking component amplitude and lifetime, and offset is a small constant. FIG. 15 shows fits to waveguides of various diameters, with good agreement between the theoretical curves and data confirming the accuracy of the effective observation volume model. These experiments, therefore, verify that zero-mode waveguides have been constructed and that they effectively confine the effective observation volume to zeptoliter dimensions.

The confinement mechanism of the zero-mode waveguide can add usefulness to many of the single-molecule spectroscopic techniques known in the art. In addition to FCS, and cross-correlation spectroscopy, the technique of dual-color cross-correlation spectroscopy is described in "Dual-color fluorescence cross-correlation spectroscopy for multicomponent diffusional analysis in solution" Schwille, P., Meyer-Almes, F. J., Rigler R. Biophys. J. Vol. 72 No. 4: pp. 1878–1886 April 1997, which is hereby incorporated by reference. This technique can be extended to function with two-photon excitation as described in "Two-photon fluorescence coincidence analysis: rapid measurements of enzyme kinetics", Heinz, K. G., Rarbach, M., Jahnz, M. and Schwille, P., Biophys J, September 2002 pp. 1671–1681 Vol. 83, No. 3 which is hereby incorporated by reference. Both of these techniques can be enhanced by the inclusion of the zero-mode waveguide as a volume limiting technique.

It will be seen by one skilled in the art of single-molecule spectroscopy and analysis that several different types of presentations of the analyte will be useful. Analytes can diffuse freely in solution or be immobilized in the illuminated region of the zero-mode waveguide. In cases where there is more than one analyte and these various analytes are expected to interact with one another, all of the permutations of bound and diffusing analytes are possible. For two analytes, both can be freely diffusing, one or the other of them can be immobilized, or both can be immobilized (such is the case where more than one fluorescent label is attached to different residues of a single amino acid chain to observe the folding kinetics of the protein). In the case of observation of enzymatic activity (see example 4 herein), it is useful to immobilize the polymerase molecule to the device, while allowing the dNTP analogs bearing the fluorescent labels to diffuse freely. In a study of DNA—DNA renaturation kinetics from P. Schwille et al 1997 above it was advantageous to have both components of the analyte diffusing freely. Many useful configurations of labels and biological molecules are outlined in "Fluorescence spectroscopy of single biomolecules", S. Weiss, Science, Vol. 283, pp. 1676–1683, which is hereby incorporated by reference. In the present invention, the zero-mode waveguide is contemplated in conjunction with all of these configurations to improve the signal-to-noise, temporal resolution and tolerance to high ligand concentration.

Example 4

Observation of Enzymatic Activity in Zero-Mode Waveguides

SEQUENASE, a commercially available exonuclease-deficient mutant of T7 DNA polymerase (USB Corporation, Cleveland, Ohio), was immobilized on the bottom of a zero-mode waveguide by 15 minute incubation of the zero-mode waveguide structure with a 1:10 dilution of the commercial stock solution (13 U/µl in 20 mM $KPO_4$, pH 7.4, 1 mM DTT, 0.1 mM EDTA, 50% glycerol) in glycerol enzyme dilution buffer (provided with the SEQUENASE enzyme, this buffer contains 20 mM Tris-HCl, pH 7.5, 2 mM DTT, 0.1 mM EDTA, 50% glycerol). The waveguide was made of a 50 nm thick aluminum film on a clean fused silica coverslip (25×25 mm square (from Esco Products, Oak Ridge, N.J.)) with an array of waveguides of different sizes. After immobilization, excess unbound enzyme was washed away by extensive flushing with 1×pH 7.5 buffer (40 mM Tris-HCl, pH 7.5, 10 mM $MgCl_2$, 10 mM NaCl). The reaction of DNA polymerization using the fluorophore coumarin-5-dCTP instead of dCTP was initiated by incubating the waveguide with a reaction mixture containing 3 ng/µl primed M13 DNA, 5 mM dithiothreitol, 7.5 µM dATP, coumarin-5-dCTP, dGTP, dTTP, 6 ng/µl single-stranded DNA binding protein in 1×pH 7.5 buffer. Primed M13 DNA was provided by annealing 2 µg of M13mp18 DNA to (−40) M13 primer (2 pmol) in a 20 µl volume of 40 mM Tris-HCl, pH 8.0, 20 mM $MgCl_2$, and 50 mM NaCl by heating for 2 minutes at 65° C. and subsequent slow cooling to <35° C. over 30 minutes.

Figure 16:
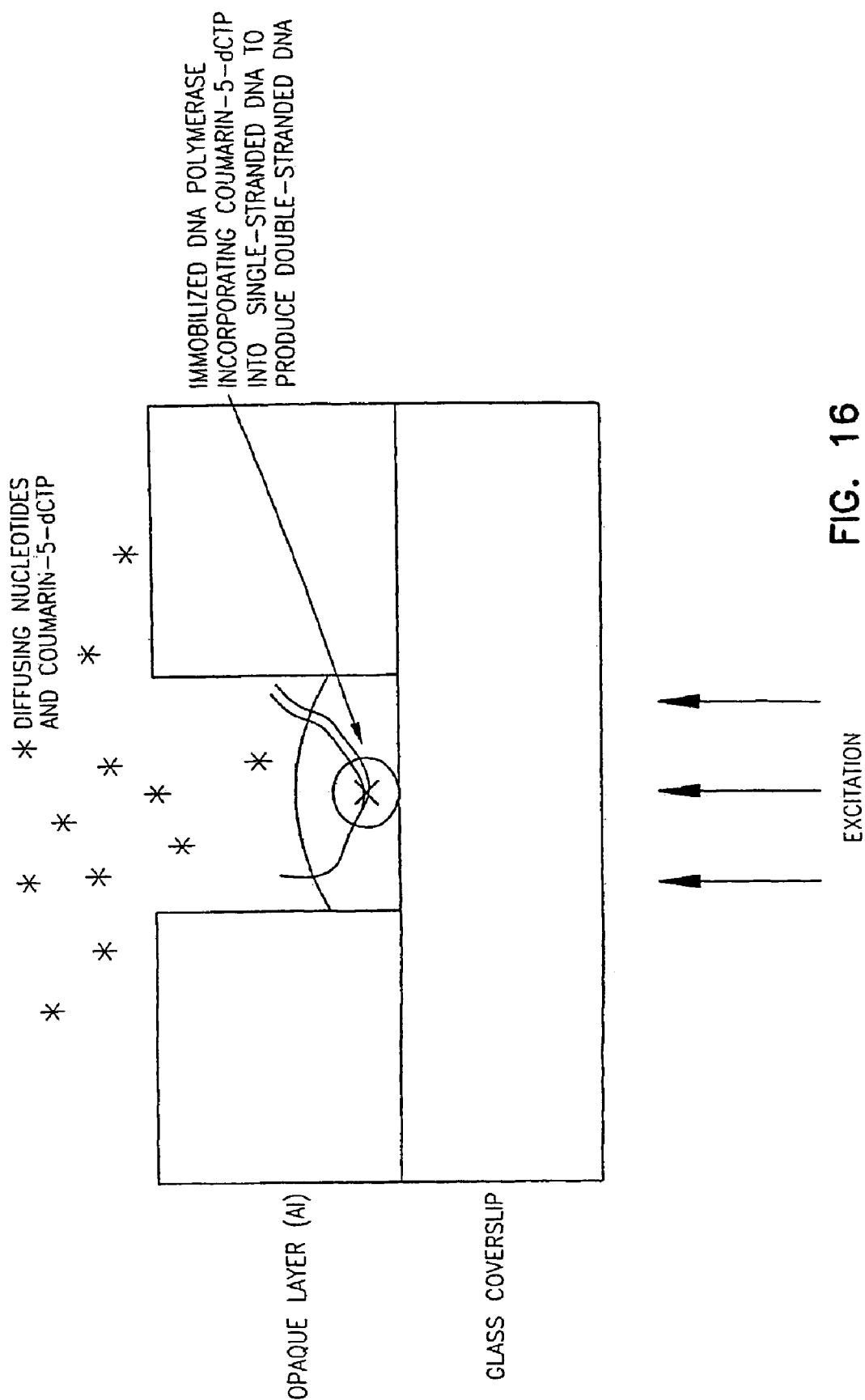
FIG. 16 is a cross-section of a zero-mode waveguide in accordance with the present invention used for observation of enzymatic activity.

As shown in FIG. 16, the zero-mode waveguide with immobilized polymerase was illuminated from the glass side with 488 nm circularly polarized light from an argon ion laser using a 60× water immersion microscope objective (UPlanApo, Olympus, Melville, N.Y., NA=1.2). Fluorescence was collected by the same objective, passed through a dichroic mirror (dichroic long-pass 500, ChromaTechnology Corp., Brattleboro, Vt.) and two emission filters (575/150 and 580/150, Chroma Technology Corp., Brattleboro, Vt.) to block reflected laser light and coupled into a 100 µm optical fiber (OZ Optics Ltd.). This fiber was used to send the signal to an avalanche photodiode (APD, Perkin Elmer Optoelectronics, Fremont, Calif.) for detection of the fluorescence photons. The signal from the APD was sent to a correlator card (Correlator.com, Bridgewater, N.J.) in a computer, where the time trace of fluorescence was recorded and stored, and the autocorrelation function of the signal was calculated.

Figure 17:
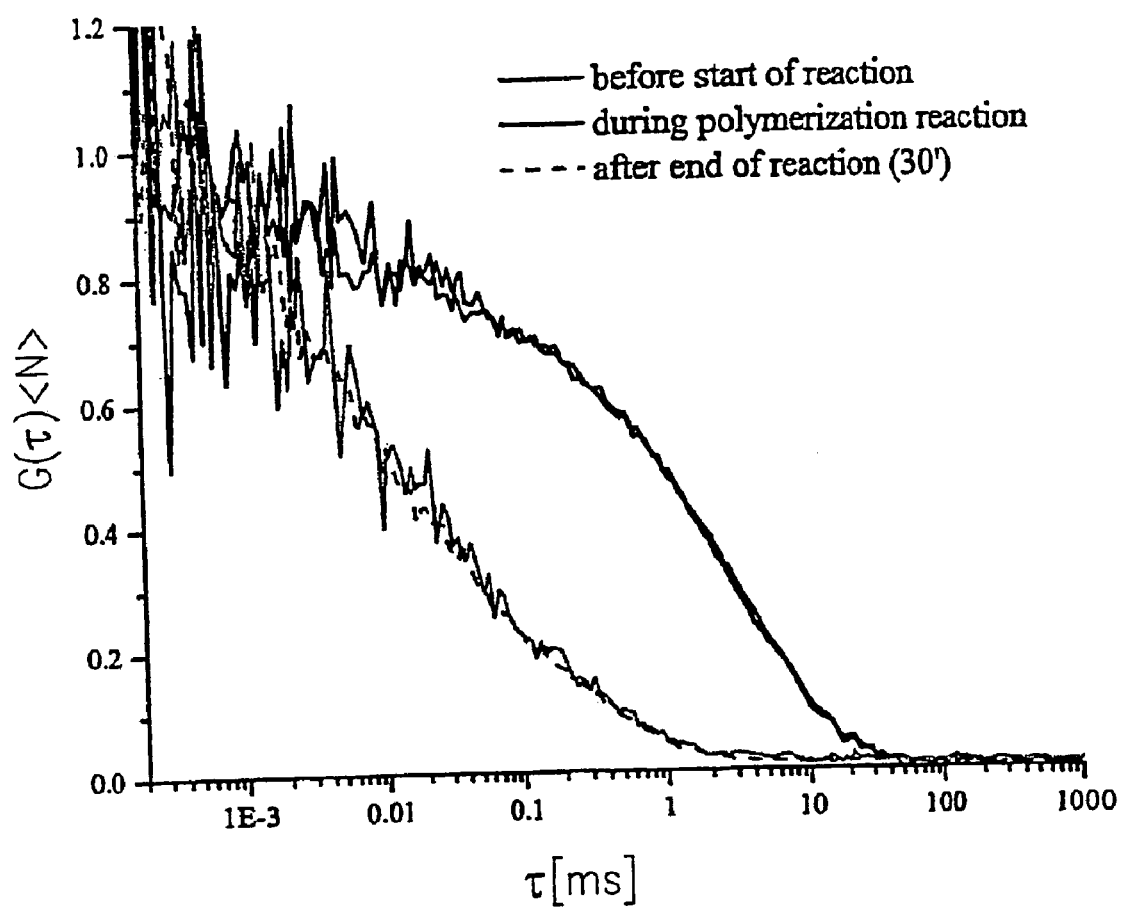
FIG. 17 shows fluorescence correlation spectroscopy ("FCS") curves from a waveguide before, during, and after use of a polymerase.

FIG. 17 shows the FCS curves from a waveguide before, during, and after the polymerization reaction. Before initiation of the polymerization reaction (gray solid curve; in the presence of 7.5 µM coumarin-5-dCTP, but in the absence of DNA), the FCS curve only shows a decay originating from the fast diffusion of the fluorescent coumarin-5-dCTP, analogous to FIG. 15 for the diffusion of Bodipy-515-PP inside zero-mode waveguides. After initiation of the polymerization reaction by addition of all ingredients necessary to support efficient DNA synthesis, FCS curves are dominated by fluctuations originating from incorporation of coumarin-5-dCTP into DNA by the enzymatic activity of DNA polymerase, with a much longer time constant of ~2 ms. This is because the coumarin-5-dCTP is incorporated into DNA which in turn is bound to the molecule of DNA polymerase, and therefore the fluorophore spends a long time in the confined volume of the zero-mode waveguide, continuously emitting fluorescence until it is photobleached. After completion of DNA polymerization (all of the single-stranded DNA has been extended into double-stranded DNA), the FCS curve returns to the shape that was obtained before initiation of the polymerization reaction (gray dashed curve).

Figure 18:
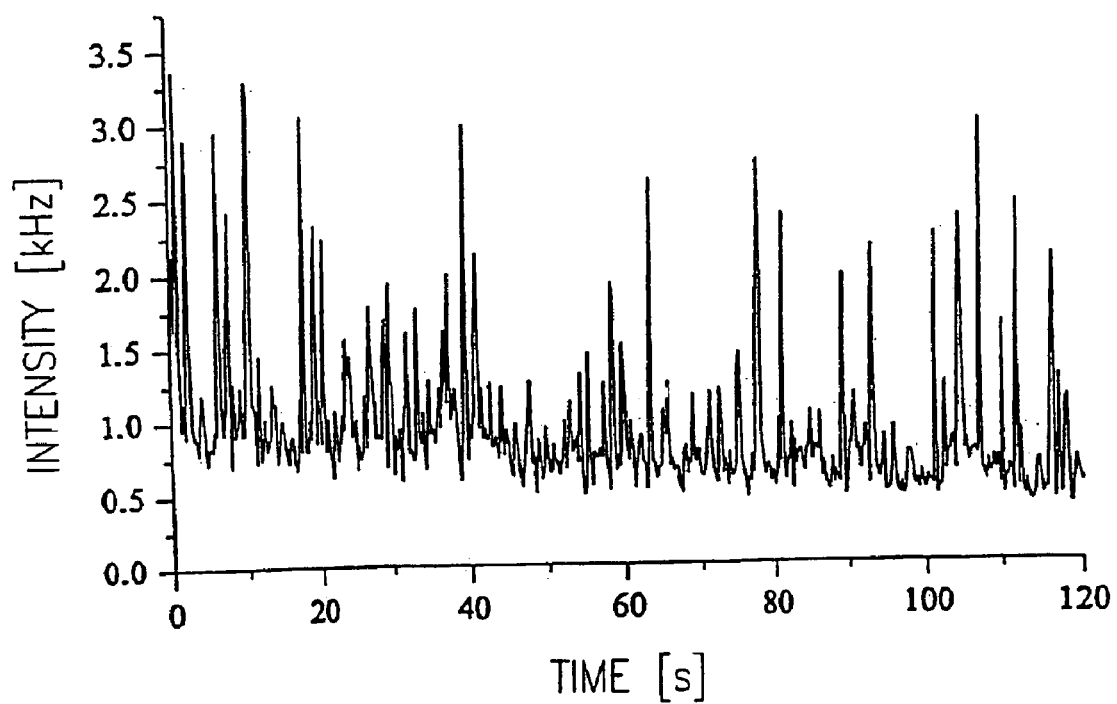
FIG. 18 shows a time trace of fluorescence during use of a polymerase.

FIG. 18 shows a time trace of fluorescence during the period of polymerization of coumarin-5-dCTP into M13 DNA. Distinct bursts of fluorescence are visible, corresponding to incorporation of a coumarin-5-dCTP molecule into DNA, and subsequent photobleaching of the fluorophore. Traces, such as shown in FIGS. 17 and 18, can be used for characterization of the DNA polymerization process on a single molecule level.

For the analysis of this example, the concentration of fluorophore (coumarin-5-dCTP) is fairly high, at 7.5 µM. The fact that single molecule enzymatic activity can be observed inside the waveguide demonstrates that the zero-mode waveguide of the present invention provides a confined volume to enable such analysis. In unconfined volumes, the number of fluorophores would be far too high to permit the observation of enzymatic turnovers of DNA polymerase. For example, in a diffraction-limited excitation volume of 0.2 fl, such as provided by focusing laser light with a high numerical aperture objective lens, a concentration of 7.5 µM corresponds to an average of ca. 900 fluorophores simultaneously present inside the volume.

Example 5

Use of a Superstructure to Enable Use of Many Samples on a Single Chip

Figure 19:
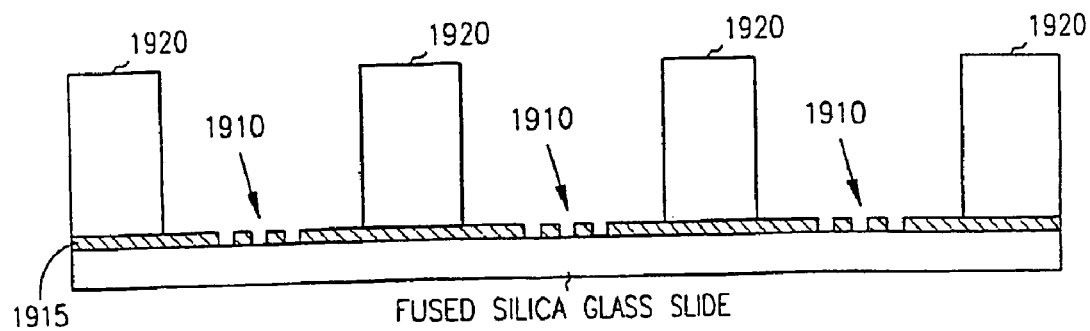
FIG. 19 is a cross-sectional view of a chip containing zero-mode waveguide devices and superstructure for isolating individual zero-mode waveguide devices in an array from one another to facilitate independent analysis of several samples on a single chip.
Figure 20:
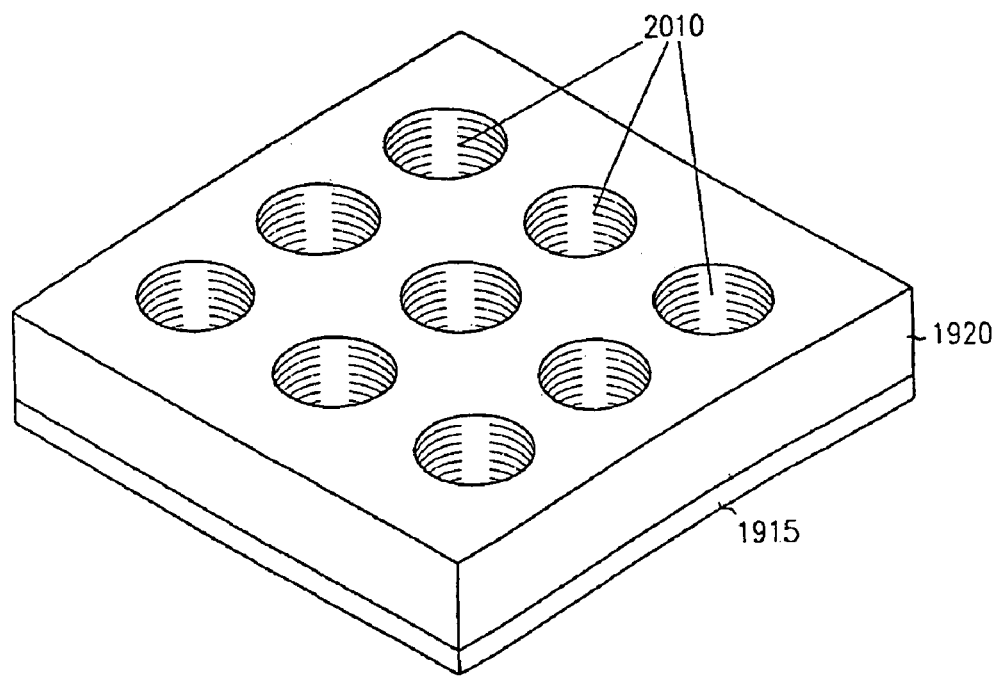
FIG. 20 is a perspective view of the device shown in FIG. 19.
Figure 21:
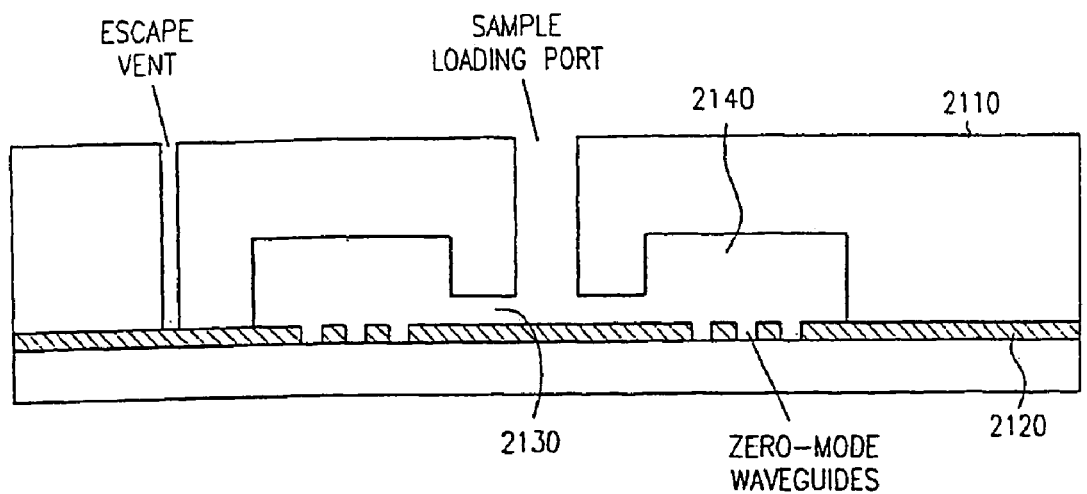
FIG. 21 is a cross-sectional view of a chip containing zero-mode waveguide devices and superstructure for delivering aliquots of a single sample to several zero-mode waveguide devices on a single chip by way of the same sample inlet port.

The zero mode waveguide devices are very small and use a minute fraction of the available surface area of a moderate-sized chip. As seen in FIG. 19, it is possible to replicate the pattern of holes indicated generally at 1910 in the aluminum film 1915 many times over on a 25 mm square fused silica chip. It is desirable to be able to apply each of these devices with a separate sample to increase the number of experiments that can be conducted with a single chip. A silicone (polydimethylsiloxane) superstructure such as silicone rubber gaskets 1920 is applied to the aluminized surface after the fabrication of the zero-mode waveguides in the metal film. The silicone structure 1920 contains an array of holes as seen in a perspective view of FIG. 19 at 2010 coincident with the centers of the zero-mode waveguide devices so that the union of these two forms wells into which a fluid sample can be placed while preventing contamination of the neighboring zero-mode waveguide devices. Such devices are commercially available from Grace Biolabs, Inc. in Bend, Oreg. Through the use of this method a single chip can be employed with dozens of separate samples. While silicone has been used for this purpose, the present invention contemplates any suitable material and means of attachment for the use of a superstructure to isolate neighboring zero-mode waveguide devices.

Example 6

Use of a Superstructure to Enable Multiple Analyses of a Single Sample

As with the previous example, a silicone superstructure 2110 is applied to the aluminized surface 2120. The silicone superstructure 2110 is patterned with grooves 2130 and rectangular recesses 2140 that when mated with the aluminized surface create fluid channels and cavities respectively. Techniques for creating microfluidic structures for application in this way are known in the art and are discussed in technical papers such as "fabrication of a configurable, single-use microfluidic device", McDonald, J. C., Metally, S. J. and Whitesides, G. M., Analytical Chemistry 73 (23): 5645–5650 Dec. 1 (2001), which is hereby incorporated by reference.

Figure 22:
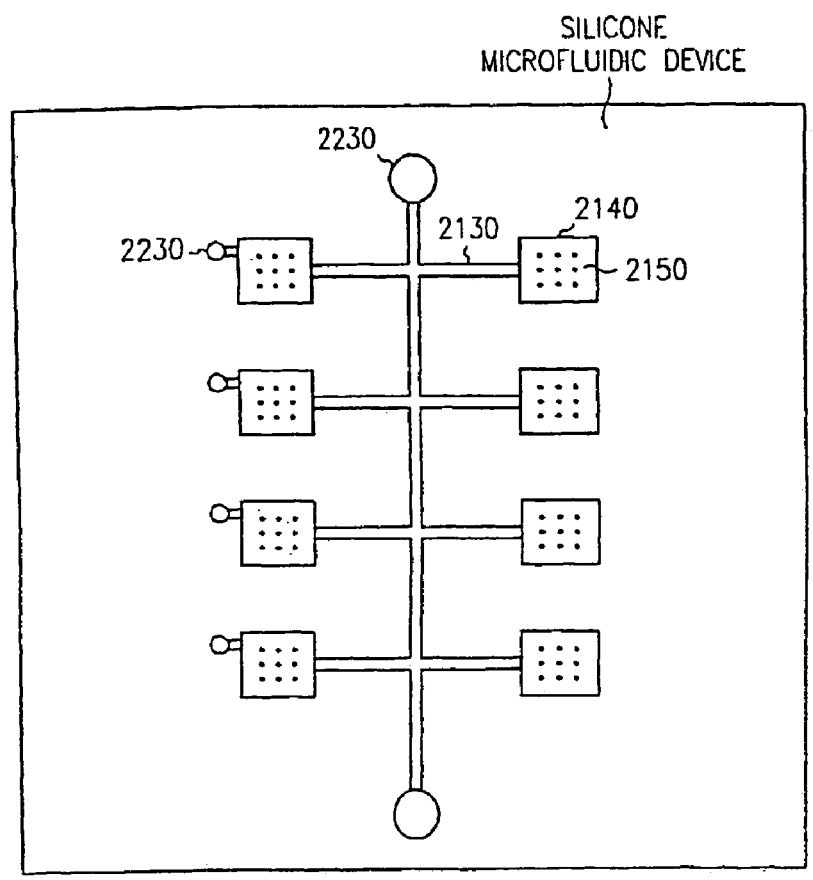
FIG. 22 is a plan view of the device depicted in FIG. 21.
Figure 23:
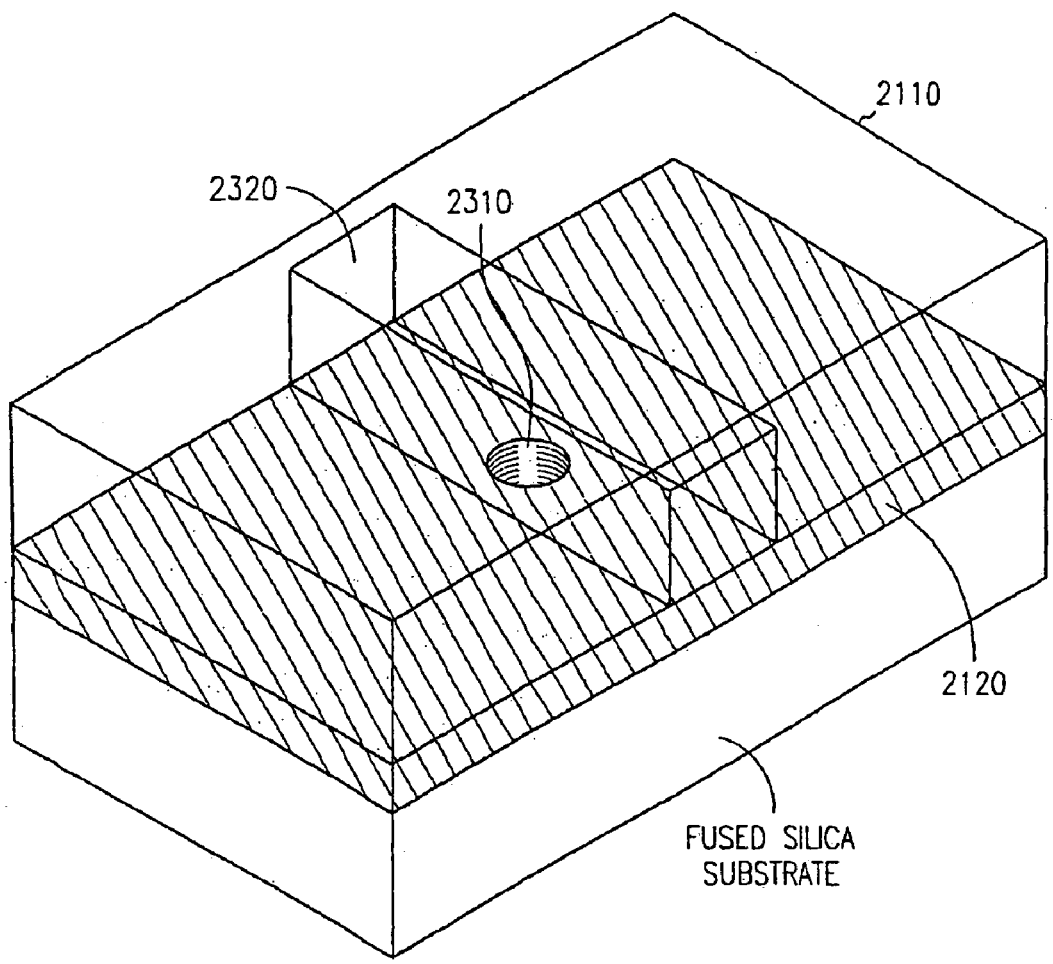
FIG. 23 is a perspective view of a zero-mode waveguide constructed in conjunction with a fluid channel to allow analysis of analytes in the channel.

FIG. 22 is a plan view of the structures. The placement of the rectangular recesses 2140 in the silicone superstructure is chosen to coincide with the locations of zero-mode waveguide devices 2150 on the fused silica chip. The fluid channels 2130 can be used simply to convey liquid to the several cavities where different analyses will take place. For example, each cavity can be pre-loaded with different reagents prior to mating the superstructure with the chip so that each cavity enables a distinct experiment on the sample. Alternatively the fluid channels can be employed to perform pre-processing of the sample before it arrives in the cavity. For example, capillary electophoresis can be performed to fractionate the sample into components before delivering these components to separate cavities containing zero-mode waveguide devices for further analysis of the sample. Zero-mode waveguides such as waveguide 2310 can also be placed to coincide with a channel 2320 as seen in FIG. 23, so as to allow analysis of material as it passes through the channel. Air vents 2230 can optionally be used in cases where trapped gas prevents the entry of fluid into the recesses or fluid channels. These air vents can also serve as conduits to allow the introduction of other materials to the cavities after the superstructure has been mated to the fused silica chip. These microfluidic channels and fluid cavities can also facilitate the use of much smaller quantities of sample than can be conveniently managed using hand-pipetting methods. While silicone has been used for this purpose, the present invention contemplates any suitable material and means of attachment for the use of a superstructure to provide microfluidic channels and fluid cavities in conjunction with zero-mode waveguides to allow multiple analyses in parallel on a single sample.

CONCLUSION

In the present invention, the region of observation is internal to the waveguide, as opposed to prior methods in which the region of observation is external to the sub-wavelength aperture. By making use of the light internal to the waveguide, the present invention achieves good light efficiency.

The extreme confinement of the effective observation volume by the zero-mode waveguide of the present invention enables a proportional increase in the limiting concentration of analytes up to which single molecule detection is still possible. This is important for many applications involving the study of single molecules. Dorre, et al., "Highly Efficient Single Molecule Detection in Microstructures," J. Biotech. 86:225–36 (2001), which is hereby incorporated by reference. As many processes, particularly many biochemical reactions, occur efficiently only at concentrations much higher than the pico- or nanomolar concentration regime typically required for single molecule analysis in solution, zero-mode waveguides offer the potential to study these processes at more appropriate concentrations, for example, under physiologically relevant conditions. With the use of zero-mode waveguides, single molecule characterization is possible at much higher concentrations, ranging into the micromolar regime, thus extending the range of biochemical reactions that can successfully be studied on a single molecule level. Zero-mode waveguides, therefore, provide the field of single molecule research with novel instrumentation so that higher concentrations of analytes can be studied and higher background can be tolerated.

In addition to permitting the use of higher concentrations, the zero-mode waveguides of the present invention permit analysis of small volumes with the feature that signal fluctuations from diffusion of analytes occurs about 100 times more rapidly than by using a volume created by high numerical aperture objective lenses. As a result, enzymatic turnovers or chemical reactions can be more confidently distinguished from diffusion. The diffusional residence time of a molecule inside the waveguide is relevant to the temporal resolution capabilities of studies of enzymatic and chemical dynamics by setting a lower limit of what time regime can be measured. Reactions that produce fluorescent products or intermediates are distinguishable from diffusional background fluorescence fluctuations if the relevant reaction rates are longer than the typical diffusion time. Thus, one can analyze faster processes than would be possible without using zero-mode waveguides.

Although the invention has been described in detail for the purposes of illustration, it is understood that such detail is solely for that purpose, and variations can be made therein by those skilled in the art without departing from the spirit and scope of the invention which is defined by the following claims.

What is claimed is:

1. A zero mode waveguide, comprising:
a substrate layer;
a cladding layer disposed upon the substrate layer; and
a core comprising a hole disposed through the cladding layer, wherein the hole is configured to substantially preclude electromagnetic energy of a frequency less than a cutoff frequency entering the core from propagating longitudinally through said zero mode waveguide.

2. The zero mode waveguide of claim 1, wherein the cladding layer comprises a metal film.

3. The zero mode waveguide of claim 2, wherein the metal film comprises a metal selected from the group consisting of aluminum, gold and chromium.

4. The zero mode waveguide of claim 1, wherein the hole comprises a diameter of less than about 100 nm.

5. The zero mode waveguide of claim 1, wherein the hole comprises a diameter that is between 1 nm and 100 nm.

6. The zero mode waveguide of claim 1, wherein the hoe comprises a diameter that is between 50 nm and 100 nm.

7. The zero mode waveguide of claim 1, wherein the hole comprises a diameter of between 30 nm and 100 nm.

8. The zero mode waveguide of claim 1, wherein the substrate is transparent.

9. The zero mode waveguide of claim 8, wherein the substrate is selected from glass and fused silica.

10. The zero mode waveguide of claim 1, further comprising a superstructure defining a well, wherein the substrate, cladding and core are disposed within the well.

11. The zero mode waveguide of claim 10, wherein the substrate, cladding and core are disposed at a bottom surface of the well.

12. A zero mode waveguide, comprising:
a transparent substrate layer;
a cladding layer disposed upon the substrate layer; and
a core comprising a hole disposed in the cladding layer, wherein the hole is dimensioned such that electromagnetic radiation entering the core provides an effective illumination volume that is substantially internal to the core of said zero mode waveguide.

13. The zero mode waveguide of claim 12, wherein electromagnetic radiation can enter the core through the transparent layer.

14. The zero mode waveguide of claim 12, wherein the cladding layer comprises a metal film.

15. The zero mode waveguide of claim 13, wherein the metal film comprises a metal selected from the group consisting of aluminum, gold and chromium.

16. The zero mode waveguide of claim 12, wherein the hole comprises a diameter of less than about 100 mm.

17. The zero mode waveguide of claim 12, wherein the hole comprises a diameter that is between 1 mm and 100 mm.

18. The zero mode waveguide of claim 12, wherein the hole comprises a diameter that is between 50 nm and 100 mm.

19. The zero mode waveguide of claim 12, wherein the hole comprises a diameter of between 30 nm and 100 nm.

20. The zero mode waveguide of claim 12, further comprising a superstructure defining a well, wherein the substrate, cladding and core are disposed within the well.

21. The zero mode waveguide of claim 12, wherein the hole is disposed completely through the cladding layer.

22. An array of zero mode waveguides, comprising
a transparent substrate layer;
a cladding layer disposed upon the substrate layer; and
a plurality of cores, wherein each of the plurality of cores comprises a hole disposed in the cladding layer and wherein the plurality of cores are configured to substantially preclude electromagnetic energy of a frequency less than a cutoff frequency entering the core from propagating longitudinally through said zero mode waveguide.

23. The array of claim 22, wherein at least one of the plurality of cores is less than about 100 nm in diameter.

24. The array of claim 22, wherein each of the plurality of cores is less than about 100 nm in diameter.

25. The array of claim 22, wherein each of the plurality of cores comprises a diameter between 1 nm and 100 nm.

26. The array of claim 22, wherein each of the plurality of cores comprises a diameter between 50 nm and 100 nm.

27. The array of claim 22, wherein each of the plurality of cores comprises a diameter between 30 nm and 100 nm.

28. The array of claim 22, further comprising a superstructure that defines a well, wherein the transparent substrate, cladding and plurality of cores are disposed at a bottom surface of the well.

29. The array of claim 28, wherein the superstructure comprises a plurality of additional wells, each of the plurality of additional wells having a separate array disposed therein, each array comprising a transparent substrate layer, a cladding layer disposed upon the substrate layer, and a plurality of cores disposed through the cladding layer, wherein each of the plurality of cores comprises a hole disposed through the cladding layer and wherein the plurality of cores are configured to substantially preclude electromagnetic energy of a frequency less than a cutoff frequency entering the core from propagating longitudinally therethrough.

30. The array of claim 22, wherein a diameter of each of the plurality of cores varies by less than 4 nm in diameter from each other of the plurality of cores.

31. The array of claim 22, wherein each of the plurality of cores is disposed completely through the cladding layer.

* * * * *

UNITED STATES PATENT AND TRADEMARK OFFICE
CERTIFICATE OF CORRECTION

PATENT NO. : 7,181,122 B1 Page 1 of 1
APPLICATION NO. : 11/313971
DATED : February 20, 2007
INVENTOR(S) : Levene et al.

It is certified that error appears in the above-identified patent and that said Letters Patent is hereby corrected as shown below:

Column 15, line 45, please change:

"hoe" to -- hole --

Signed and Sealed this

Twenty-fourth Day of April, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,181,122 B1 | Page 1 of 1 |
| APPLICATION NO. | : 11/313971 | |
| DATED | : February 20, 2007 | |
| INVENTOR(S) | : Michael J. Levene et al. | |

It is certified that error appears in the above-identified patent and that said Letters Patent is hereby corrected as shown below:

Column 1, line 17, please delete "066898-0003891. The U.S. Government may have" and insert -- DE-FG02-99ER62809. The Government has --, Signed and Sealed this
First Day of March, 2011

David J. Kappos
*Director of the United States Patent and Trademark Office*